US008148376B2

(12) United States Patent
Chisholm et al.

(10) Patent No.: US 8,148,376 B2
(45) Date of Patent: Apr. 3, 2012

(54) 3,4-DIHYDROQUINOXALIN-2(1H)-ONES FOR USE AS STEAROYL COA DESATURASE INHIBITORS

(75) Inventors: Jeffrey Chisholm, Mountain View, CA (US); Dmitry Koltun, Foster City, CA (US); Jeff Zablocki, Los Altos, CA (US); Eric Parkhill, San Francisco, CA (US); Andrey Glushkov, Moscow (RU); Natalya Vasilevich, Moscow (RU); Timur Zilbershtein, Tomsk (RU); Alexey Ivanov, Moscow (RU)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 12/767,515

(22) Filed: Apr. 26, 2010

(65) Prior Publication Data
US 2010/0204238 A1 Aug. 12, 2010

Related U.S. Application Data

(62) Division of application No. 11/868,386, filed on Oct. 5, 2007, now Pat. No. 7,732,453.

(60) Provisional application No. 60/849,648, filed on Oct. 5, 2006.

(51) Int. Cl.
*A61K 31/495* (2006.01)
(52) U.S. Cl. ......... 514/249; 544/350; 544/354; 546/187
(58) Field of Classification Search .................. 514/249; 544/350, 354; 546/187
See application file for complete search history.

(56) References Cited

U.S. PATENT DOCUMENTS

| | | | |
|---|---|---|---|
| 3,845,770 A | 11/1974 | Theeuwes et al. |
| 4,326,525 A | 4/1982 | Swanson et al. |
| 4,992,445 A | 2/1991 | Lawter et al. |
| 5,001,139 A | 3/1991 | Lawter et al. |
| 5,023,252 A | 6/1991 | Hseih |
| 5,616,345 A | 4/1997 | Geoghegan et al. |
| 7,196,090 B2 | 3/2007 | Connolly et al. |
| 2004/0019210 A1 | 1/2004 | Chivikas Connolly et al. |
| 2004/0142950 A1 | 7/2004 | Bunker et al. |
| 2006/0223741 A1 | 10/2006 | Smith et al. |
| 2008/0139570 A1 | 6/2008 | Chisholm et al. |
| 2008/0249100 A1 | 10/2008 | Chisholm et al. |
| 2008/0255130 A1 | 10/2008 | Koltun et al. |
| 2008/0255161 A1 | 10/2008 | Koltun et al. |
| 2009/0105283 A1 | 4/2009 | Koltun et al. |
| 2009/0253704 A1 | 10/2009 | Koltun et al. |
| 2009/0253738 A1 | 10/2009 | Koltun et al. |
| 2010/0113463 A1 | 5/2010 | Chisholm et al. |

FOREIGN PATENT DOCUMENTS

| | | |
|---|---|---|
| CN | 1308536 A | 8/2001 |
| CN | 1738806 A | 2/2006 |
| EP | 0411766 A1 | 2/1991 |
| WO | WO-9950254 A1 | 10/1999 |
| WO | WO-0119825 A1 | 3/2001 |
| WO | WO 2008/043087 * | 4/2008 |

OTHER PUBLICATIONS

Office Action for European Patent Application No. 07-853 820.4-2117, mailed Dec. 21, 2010.
Office Action for New Zealand Patent Application No. 576038, mailed Aug. 16, 2010.
Office Action for Chinese Application No. 20080011238.7, mailed Apr. 8, 2011.
De Laszlo, Stephen E. et al. (1996) "The Design, Binding Affinity Prediction and Synthesis of Macrocyclic Angiotensin II AT$_1$ and AT$_2$ Receptor Antagonists", *Bioorrganic & Medicinal Chemistry Letters*, vol. 6, pp. 923-928.
Wan, Yiqian et al. (2004) "First Reported Nonpeptide AT$_1$ Receptor Agonist (L-162,313) Acts as an AT$_2$ Receptor Agonist in Vivo", *J. Medicial Chemistry*, vol. 47, pp. 1536-1546.
Office Action for Chinese Patent Application No. 2008800112387 mailed Feb. 14, 2004.
A. Dobrzyn and J.M. Ntambi, Obes. Rev. 6, (2005), 169-174.
Chisholm, et al., The LXR Ligand T0901317 Induces Severe Lipogenesis in the db/db Diabetic Mouse; J Lipid Res., vol. 44, No. 11, 2003; 2039-2048.
Dorwald, F. Zaragoza. Side Reactions in Organic Synthesis: A Guide to Successful Synthesis Design, Weinheim: Wiley-VCH Verlag GmbH & Co. KGaA, 2005, Preface.
Gutierrez-Juarez et al. Critical Role of Stearoyl-CoA Desaturase—1 (SCD1) in the Onset of Diet-Induced Hepatic Insulin Resistance (2006) J. Clin. Invest. 116:1686-1695.
International Search Report for PCT/US2007/080627, International Filing Date Oct. 5, 2007, mailed Mar. 31, 2008.
Jiang et al. Prevention of Obesity in Mice by Antisense Oligonucleotide Inhibitors of Stearoyl-CoA Desaturase—1 (2005) J. Clin. Invest. 115:1030-1038.
Jordan, V. C. Nature Reviews: Drug Discovery, 2, 2003, p. 205.
Ntambi et al. (2004) Prog Lipid Res 43, 91-104; (2005).
Remington's Pharmaceutical Sciences, Mace Publishing Co., Philadelphia, PA 17.sup.th Ed. (1985).
Talamo and Bloch (1969) Analytical Biochemistry 29:300-304.
U.S. Appl. No. 12/579,139, filed Oct. 14, 2009.
U.S. Appl. No. 12/579,231, filed Oct. 14, 2009.
Vippagunta, et al. Advanced Drug Delivery Reviews, 48, 2001, p. 18.
Wolff, Manfred E., Ed. Burger's Medicinal Chemistry and Drug Discovery—Fifth Edition, New York: John Wiley & Sons, 1996, vol. 1, pp. 975-976.

* cited by examiner

*Primary Examiner* — James O Wilson
*Assistant Examiner* — Douglas M Willis
(74) *Attorney, Agent, or Firm* — J. Elin Hartrum

(57) ABSTRACT

The present invention discloses 3,4-dihydroquinoxalin-2 (1H)-ones for use as inhibitors of stearoyl-CoA desaturase. The compounds are useful in treating and/or preventing various human diseases, mediated by stearoyl-CoA desaturase (SCD) enzymes, especially diseases related to abnormal lipid levels, cardiovascular disease, diabetes, obesity, oily skin conditions, metabolic syndrome, and the like.

15 Claims, No Drawings

3, 4-DIHYDROQUINOXALIN-2(1H)-ONES FOR USE AS STEAROYL COA DESATURASE INHIBITORS

CROSS-REFERENCE TO RELATED APPLICATIONS

This application is a Divisional of U.S. patent application Ser. No. 11/868,386, filed Oct. 5, 2007 now U.S. Pat. No. 7,732,453 which claims priority to U.S. Provisional Patent Application Ser. No. 60/849,648, filed Oct. 5, 2006, the entirety of which is incorporated herein by reference.

FIELD OF THE INVENTION

The present invention relates generally to the field of inhibitors of stearoyl-CoA desaturase, such as pyridine[2,3-b]pyrazone derivatives, pyrido[4,3-b]pyrazin-2(1H)-one derivatives, and quinoxalin-2(1H)-one derivatives, and uses for such compounds in treating and/or preventing various human diseases, mediated by stearoyl-CoA desaturase (SCD) enzymes, especially diseases related to elevated lipid levels, cardiovascular disease, cancer, diabetes, obesity, metabolic syndrome, oily skin conditions, and the like.

BACKGROUND

Stearoyl CoA desaturases (SCD's) are Δ9 fatty acid desaturases. The mammalian enzymes are localized to the endoplasmic reticulum and require molecular $O_2$ and NADH to desaturate saturated fatty acids at the Δ9 position and generate monounsaturated fatty acids and water in the process. The primary substrates for these enzymes are the acyl-CoA derivatives of stearic (C18) and palmitic acids (C16) with the major reaction being the conversion of stearic acid to oleate (C18:1). Depending on the species, 2-4 isoforms of SCD exist. In rodents these isoforms are highly homologous and differ primarily in tissue distribution. In humans there are 2 known isoforms (SCD1 and SCD5) and these isoforms function similarly, but SCD5 has reduced sequence homology to other SCD isoforms. Based on tissue distribution SCD5 appears to functionally analogous to rodent SCD2.

The best characterized SCD isozyme is SCD1 which is primarily found in liver, adipose and skeletal muscle. Deletion, mutation or inhibition of SCD1 in mice and rats results in decreased hepatic triglyceride secretion, decreased hepatic triglycerides and steatosis, resistance to weight gain and improvements in insulin sensitivity and glucose uptake (reviewed in Ntarnbi et al. (2004) *Prog Lipid Res* 43, 91-104; (2005), *Prostaglandins Leukot. Essent. Fatty Acids* 73, 35-41; and (2005) *Obes. Rev.* 6, 169-174. These studies combined with studies in humans showing correlations between surrogates for SCD activity and obesity strongly implicate SCD inhibition as a means to treat obesity, hypertryglyceridemia and associated diseases and co-morbidities. Studies done using antisense oligonucleotide inhibitors have also confirmed the results of the SCD1 knockout and asebia mouse studies, and clearly shown that hepatic SCD inhibition may reduce elevated hepatic glucose output; see Jiang et al. (2005) *J. Clin. Invest.* 115:1030-1038G. and Gutierrez-Juarez et al. (2006) *J. Clin. Invest.* 116:1686-1695.

The present invention presents compounds that are useful in inhibiting SCD activity and thus regulating tissue and plasma lipid levels and fatty acid composition. These compounds are useful in the treatment of SCD-mediated diseases such as diseases related to dyslipidemia and disorders of lipid metabolism, including, but not limited to diseases related to elevated lipid levels, cardiovascular disease, diabetes, obesity, metabolic syndrome, fatty liver diseases, and the like.

SUMMARY OF THE INVENTION

It is an object of this invention to provide compounds that act as stearoyl-CoA desaturase inhibitors. Accordingly, in a first aspect, the invention relates to compounds of Formula I:

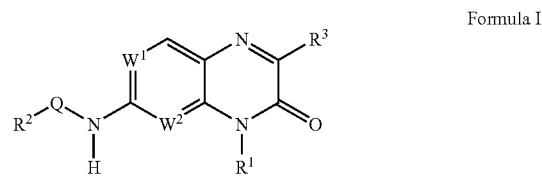

Formula I wherein
$R^1$ is
a) optionally substituted 4 to 6 membered nitrogen containing monocyclic heterocycle,
b) —X—$NR^4R^5$,
c) —X—C(O)$NR^4R^5$,
d) —X—C(O)$OR^7$, or
e) —X—$OR^7$
wherein
$R^4$ is hydrogen or $C_{1-4}$ lower alkyl, and
$R^5$ is hydrogen, $C_{1-4}$ lower alkyl, aryl, heteroaryl, $C_{1-4}$ alkoxy, —C(=NH)$NH_2$, —C(=O)$R^6$ or —S(=O)$_2R^6$, wherein
$R^6$ is hydrogen, optionally substituted $C_{1-4}$ alkyl, optionally substituted $C_{1-4}$ alkenyl, $C_{1-4}$ alkoxy, 5 or 6 membered optionally substituted monocyclic aryl, or 5 or 6 membered optionally substituted monocyclic heteroaryl, or
$R^4$ and $R^5$ along with the nitrogen to which they are attached join to form a 5 or 6 membered monocyclic heteroaryl or heteroalkyl ring;
$R^7$ is hydrogen, optionally substituted $C_{1-4}$ alkyl, optionally substituted $C_{1-4}$ alkenyl, 5 or 6 membered optionally substituted monocyclic aryl, or 5 or 6 membered optionally substituted monocyclic heteroaryl,
X is optionally substituted $C_{2-4}$ linear or branched alkylene;
$R^2$ is optionally substituted mono or bicyclic heterocyclyl, mono or bicyclic aryl, or mono or bicyclic heteroaryl;
wherein the aryl, heterocyclyl or heteroaryl moiety is optionally substituted with from 1 to 3 substituents independently selected from the group consisting of alkyl, heterocyclyl, aryl, heteroaryl, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $S(O)_3R^{20}$, $P(O)(OR^{20})_2$, $SO_2NR^{20}COR^{22}$, $SO_2NR^{20}CO_2R^{22}$, $SO_2NR^{20}CON(R^{20})_2$, $NR^{20}COR^{22}$, $NR^{20}CO_3R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NeSO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$, and
further wherein each optional alkyl, heteroaryl, aryl, and heterocyclyl substituent is further optionally substituted with halo, $NO_2$, alkyl, $CF_3$, amino, mono- or di-alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $S(O)_3R^{20}$, $P(O)(OR^2)_7$, $SR^{20}$, $S(O)R^{22}$, $SO_2R^{22}$, $SO_2N(R^{20})_2$, CN, or $OR^{20}$;

R³ is hydrogen, optionally substituted C$_{1-4}$ alkyl, 5 or 6 membered optionally substituted monocyclic cycloalkyl, 5 or 6 membered optionally substituted monocyclic aryl, 5 or 6 membered optionally substituted monocyclic heterocycle, or 5 or 6 membered optionally substituted monocyclic heteroaryl;

wherein the alkyl, cycloalkyl, aryl, heterocyclyl or heteroaryl moiety is optionally substituted with from 1 to 3 substituents independently selected from the group consisting of alkyl, heterocyclyl, aryl, heteroaryl, halo, NO$_2$, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, S(O)$_3$R$^{20}$, P(O)(OR$^2$)$_2$, SO$_2$NR$^{20}$COR$^{22}$, SO$_2$NR$^{20}$CO$_2$R$^{22}$, SO$_2$NR$^{20}$CON(R$^{20}$)$_2$, NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{26}$SO$_2$R$^{22}$, NR$^{20}$SO$_2$R$^{22}$, SO$_2$NR$^{26}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$, and further wherein each optional alkyl, heteroaryl, aryl, and heterocyclyl substituent is further optionally substituted with halo, NO$_2$, alkyl, CF$_3$, amino, mono- or di-alkylamino, alkyl or aryl or heteroaryl amide, NR$^{20}$COR$^{22}$, NR$^{20}$SO$_2$R$^{22}$, COR$^{20}$, CO$_2$R$^{20}$, CON(R$^{20}$)$_2$, NR$^{20}$CON(R$^{20}$)$_2$, OC(O)R$^{20}$, OC(O)N(R$^{20}$)$_2$, S(O)$_3$R$^{20}$, P(O)(OR$^{20}$)$_2$, SR$^{20}$, S(O)R$^{22}$, SO$_2$R$^{22}$, SO$_2$N(R$^{20}$)$_2$, CN, or OR$^{20}$;

R$^{20}$ and R$^{22}$ are independently selected from the group consisting of hydrogen, C$_{1-15}$ alkyl, C$_{2-15}$ alkenyl, C$_{2-15}$ alkynyl, heterocyclyl, aryl, and heteroaryl, wherein the alkyl, alkenyl, alkynyl, heterocyclyl, aryl, and heteroaryl moieties are optionally substituted with from 1 to 3 substituents independently selected from halo, alkyl, mono- or dialkylamino, alkyl or aryl or heteroaryl amide, CN, O—C$_{1-6}$ alkyl, CF$_3$, aryl, and heteroaryl;

Q is C$_{1-4}$ alkylene which may optionally contain one or more —NH—, —O—, —S—, or carbonyl linking moieties; and W$^1$ and W$^2$ are independently N or CH with the proviso that W$^1$ and W$^2$ cannot both be N, or a pharmaceutically acceptable salt, ester, prodrug, or hydrate thereof.

In yet another aspect of the invention, pharmaceutical formulations are provided, comprising a therapeutically effective amount of an SCD inhibitory compound of Formula I, and at least one pharmaceutically acceptable carrier. The formulation is preferably for oral administration.

In a third embodiment of the invention, methods of using the compounds of Formula I in the treatment of a disease or condition in a mammal that can be treated with an SCD inhibitory compound are provided. The method comprises administering to a mammal in need thereof a therapeutically effective dose of a compound of Formula I. Such diseases include, but are not limited to, cardiovascular diseases (including, but not limited to, coronary artery disease, atherosclerosis, heart disease, hypertension, and peripheral vascular disease), cancer, cerebrovascular diseases (including, but not limited to, stroke, ischemic stroke and transient ischemic attack (TIA), and ischemic retinopathy), dyslipidemia, fatty liver diseases, obesity, diabetes, insulin resistance, decreased glucose tolerance, non-insulin-dependent diabetes mellitus, Type II diabetes, Type I diabetes, and other diabetic complications.

At present, the preferred compounds for use in the invention include, but are not limited to:

N-[2-(6-{[(3,4-dichlorophenyl)methyl]amino}-2-(4-methoxyphenyl)-3-oxo-4-hydropyridino[2,3-b]pyrazin-4-yl)ethyl]acetamide;

N-[2-(6-{[(4-fluorophenyl)methyl]amino}-2-(4-methoxyphenyl)-3-oxo-4-hydropyridino[2,3-b]pyrazin-4-yl)ethyl]acetamide;

N-[2-(6-{[(3-chlorophenyl)methyl]amino}-2-(4-methoxyphenyl)-3-oxo-4-hydropyridino[2,3-b]pyrazin-4-yl)ethyl]acetamide;

N-[2-(6-{[(3-chloro-4-fluorophenyl)methyl]amino}-2-(4-methoxyphenyl)-3-oxo-4-hydropyridino[2,3-b]pyrazin-4-yl)ethyl]acetamide;

4-(2-aminoethyl)-6-{[(3,4-dichlorophenyl)methyl]amino}-2-(4-methoxyphenyl)-4-hydropyridino[3,2-b]pyrazin-3-one;

N-[2-(6-{[(3,4-dichlorophenyl)methyl]amino}-2-(4-methoxyphenyl)-3-oxo-4-hydropyridino[2,3-b]pyrazin-4-yl)ethyl]carboxamide;

N-[2-(6-{[(3,4-dichlorophenyl)methyl]amino}-3-oxo-2-(3-pyridyl)-4-hydropyridino[2,3-b]pyrazin-4-yl)ethyl]acetamide;

3-(6-{[(3,4-dichlorophenyl)methyl]amino}-2-(4-methoxyphenyl)-3-oxo-4-hydropyridino[2,3-b]pyrazin-4-yl)propanamide;

N-{2-[2-(4-methoxyphenyl)-3-oxo-6-({[3-(trifluoromethyl)phenyl]methyl}amino)-4-hydropyridino[2,3-b]pyrazin-4-yl]ethyl}acetamide;

N-{2-[2-(4-methoxyphenyl)-3-oxo-6-({[4-(trifluoromethyl)phenyl]methyl}amino)-4-hydropyridino[2,3-b]pyrazin-4-yl]ethyl}acetamide;

N-[2-(6-{[(3,4-dichlorophenyl)methyl]amino}-2-(4-methylthiophenyl)-3-oxo-4-hydropyridino[2,3-b]pyrazin-4-yl)ethyl]acetamide;

N-[2-(6-{[(3,4-dichlorophenyl)methyl]amino}-2-(4-methylphenyl)-3-oxo-4-hydropyridino[2,3-b]pyrazin-4-yl)ethyl]acetamide;

4-((3S)pyrrolidin-3-yl)-6-{[(3,4-dichlorophenyl)methyl]amino}-2-(4-methoxyphenyl)-4-hydropyridino[3,2-b]pyrazin-3-one;

N-[2-(6-{[(3-chloro-4-fluorophenyl)methyl]amino}-3-oxo-2-(3-pyridyl)-4-hydropyridino[2,3-b]pyrazin-4-yl)ethyl]acetamide;

ethyl 3-(6-{[(3,4-dichlorophenyl)methyl]amino}-2-(4-methoxyphenyl)-3-oxo-4-hydropyridino[2,3-b]pyrazin-4-yl)propanoate;

ethyl 4-(6-{[(3,4-dichlorophenyl)methyl]amino}-2-(4-methoxyphenyl)-3-oxo-4-hydropyridino[2,3-b]pyrazin-4-yl)butanoate;

4-(6-{[(3,4-dichlorophenyl)methyl]amino}-2-(4-methoxyphenyl)-3-oxo-4-hydropyridino[2,3-b]pyrazin-4-yl)butanoic acid;

3-(6-{[(3,4-dichlorophenyl)methyl]amino}-2-(4-methoxyphenyl)-3-oxo-4-hydropyridino[2,3-b]pyrazin-4-yl)propanoic acid;

3-(6-{[(3,4-dichlorophenyl)rn ethyl]amino}-3-oxo-2-(3-pyridyl)-4-hydropyridino[2,3-b]pyrazin-4-yl)propanamide;

N-[2-(6-{[(3,4-dichlorophenyl)methyl]amino}-3-oxo-2-(3-pyridyl)-4-hydropyridino[2,3-b]pyrazin-4-yl)ethyl]carboxamide;

N-{2-[3-oxo-2-(3-pyrid yl)-6-({[3-(trifluoromethyl)phen yl]methyl}amino)-4-hydropyridino[2,3-b]pyrazin-4-yl]ethyl}acetamide;

N-[2-(6-{[(3-bromophenyl)methyl]amino}-2-(4-methoxyphenyl)-3-oxo-4-hydropyridino[2,3-b]pyrazin-4-yl)ethyl]acetamide;

N-{2-[6-({[3,5-bis(trifluoromethyl)phenyl]methyl}amino)-2-(4-methoxyphenyl)-3-oxo-4-hydropyridino[2,3-b]pyrazin-4-yl]ethyl}acetamide;

N-{2-[6-({[4-fluoro-3-(trifluoromethyl)phenyl]methyl}amino)-2-(4-methoxyphenyl)-3-oxo-4-hydropyridino[2,3-b]pyrazin-4-yl]ethyl}acetamide;

4-(2-hydroxyethyl)-2-(4-methoxyphenyl)-6-({[3-(trifluoromethyl)phenyl]methyl}amino)-4-hydropyridino[3,2-b]pyrazin-3-one;

N-{2-[2-(4-methoxyphenyl)-3-oxo-6-({[5-(trifluoromethyl)(3 pyridyl)]methyl}amino)-4-hydropyridino[2,3-b]pyrazin-4-yl]ethyl}acetamide;

N-{2-[2-(4-methoxyphenyl)-3-oxo-6-({[3-(trifluoromethyl)phenyl]methyl}amino)-4-hydropyridino[2,3-b]pyrazin-4-yl]ethyl}carboxamide;

N-{2-[3-oxo-2-(3-pyridyl)-6-({[3-(trifluoromethyl)phenyl]methyl}amino)-4-hydropyridino[2,3-b]pyrazin-4-yl]ethyl}carboxamide;

N-{2-[3-oxo-2-(trifluoromethyl)-6-({[3-(trifluoromethyl)phenyl]methyl}amino)-4-hydropyridino[2,3-b]pyrazin-4-yl]ethyl}acetamide;

N-{2-[2-methyl-3-oxo-6-({[3-(trifluoromethyl)phenyl]methyl}amino)-4-hydropyridino[2,3-b]pyrazin-4-yl]ethyl}acetamide;

N-[2-(6-{[(3,4-dichlorophenyl)methyl]amino}-2-methyl-3-oxo-4-hydropyridino[2,3-b]pyrazin-4-yl)ethyl]acetamide;

3-[3-oxo-2-(3-pyridyl)-6-({[3-(trifluoromethyl)phenyl]methyl}amino)-4-hydropyridino[2,3-b]pyrazin-4-yl]propanamide;

3-[2-(4-methoxyphenyl)-3-oxo-6-({[3-(trifluoromethyl)phenyl]methyl}amino)-4-hydropyridino[2,3-b]pyrazin-4-yl]propanamide;

N-{2-[3-oxo-6-({[3-(trifluoromethyl)phenyl]methyl}amino)-4-hydropyridino[2,3-b]pyrazin-4-yl]ethyl}acetamide;

N-(2-{2-(4-methoxyphenyl)-3-oxo-6-[benzylamino]-4-hydropyridino[2,3-b]pyrazin-4-yl}ethyl)acetamide;

N-(2-{2-(4-methoxyphenyl)-3-oxo-6-[(3-pyridylmethyl)amino]-4-hydropyridino[2,3-b]pyrazin-4-yl}ethyl)acetamide;

N-[2-(6-{[(3-fluorophenyl)methyl]amino}-2-(4-methoxyphenyl)-3-oxo-4-hydropyridino[2,3-b]pyrazin-4-yl)ethyl]acetamide;

4-(6-{[(3,4-dichlorophenyl)methyl]amino}-2-(4-methoxyphenyl)-3-oxo(4-hydropyridino[2,3-b]pyrazin-4-yl))-N-methylbutanamide;

4-(6-{[(3,4-dichlorophenyl)methyl]amino}-2-(4-methoxyphenyl)-3-oxo-4-hydropyridino[2,3-b]pyrazin-4-yl)butanamide;

3-(6-{[(3,4-dichlorophenyl)methyl]amino}-2-(4-methoxyphenyl)-3-oxo(4-hydropyridino[2,3-b]pyrazin-4-yl))-N-methylpropanamide;

N-[2-(6-{[(3,4-dichlorophenyl)methyl]amino}-2-(4-methoxyphenyl)-3-oxo(4-hydropyridino[2,3-b]pyrazin-4-yl))ethyl](tert-butoxy)carboxamide;

N-[2-(6-{[(2-chlorophenyl)methyl]amino}-2-(4-methoxyphenyl)-3-oxo-4-hydropyridino[2,3-b]pyrazin-4-yl)ethyl]acetamide;

N-(2-{2-(4-methoxyphenyl)-3-oxo-6-[(3-phenylpropyl)amino]-4-hydropyridino[2,3-b]pyrazin-4-yl}ethyl)acetamide;

4-((3R)pyrrolidin-3-yl)-6-{[(3,4-dichlorophenyl)methyl]amino}-2-(4-methoxyphenyl)-4-hydropyridino[3,2-b]pyrazin-3-one;

(3R)-3-(6-{[(3,4-dichlorophenyl)methyl]amino}-2-(4-methoxyphenyl)-3-oxo(4-hydropyridino[2,3-b]pyrazin-4-yl))pyrrolidinecarbaldehyde;

(3S)-3-(6-{[(3,4-dichlorophenyl)methyl]amino}-2-(4-methoxyphenyl)-3-oxo(4-hydropyridino[2,3-b]pyrazin-4-yl))pyrrolidinecarbaldehyde;

N-{2-[2-(4-methoxyphenyl)-3-oxo-6-({[6-(trifluoromethyl)(2-pyridyl)]methyl}amino)-4-hydropyridino[2,3-b]pyrazin-4-yl]ethyl}acetamide;

N-[2-(4-methoxyphenyl)-6-{[(5-methyl(1,2,4-oxadiazol-3-yl))methyl]amino}-3-oxo-4-hydropyridino[2,3-b]pyrazin-4-yl)ethyl]acetamide;

N-[2-(4-methoxyphenyl)-6-{[(3-methoxyphenyl)methyl]amino}-3-oxo-4-hydropyridino[2,3-b]pyrazin-4-yl)ethyl]acetamide;

N-[2-(6-{[(3,4-dichlorophenyl)methyl]amino}-4-hydropyridino[2,3-b]pyrazin-4-yl)ethyl]acetamide;

methyl 3-[({4-[2-(acetylamino)ethyl]-2-(4-methoxyphenyl)-3-oxo-4-hydropyridino[5,6-b]pyrazin-6-yl}amino)methyl]benzoate;

3-[({4-[2-(acetylamino)ethyl]-2-(4-methoxyphenyl)-3-oxo-4-hydropyridino[5,6-b]pyrazin-6-yl}amino)methyl]benzoic acid;

3-[2-(4-methoxyphenyl)-3-oxo-6-({[3-(trifluoromethyl)phenyl]methyl}amino)(4-hydropyridino[2,3-b]pyrazin-4-yl)]-N-(phenylmethoxy)propanamide;

N-methoxy-3-[2-(4-methoxyphenyl)-3-oxo-6-({[3-(trifluoromethyl)phenyl]methyl}amino)(4-hydropyridino[2,3-b]pyrazin-4-yl)]propanamide;

ethyl 4-[2-(acetylamino)ethyl]-3-oxo-6-({[3-(trifluoromethyl)phenyl]methyl}amino)-4-hydropyridino[2,3-e]pyrazine-2-carboxylate;

-[2-(2-(4-methoxyphenyl)-6-({[(3-methylphenyl)methyl]amino)-3-oxo-4-hydropyridino[2,3-b]pyrazin-4-yl)ethyl]acetamide;

3-[2-(4-methoxyphenyl)-3-oxo-6-({[3-(trifluoromethyl)phenyl]methyl}amino)(4-hydropyridino[2,3-b]pyrazin-4-yl)]-N-methylpropanamide;

3-[2-(4-methoxyphenyl)-3-oxo-6-({[3-(trifluoromethyl)phenyl]methyl}amino)-4-hydropyridino[2,3-b]pyrazin-4-yl]propanehydroxamic acid;

N-{2-[2-(4-methoxyphenyl)-3-oxo-6-({[3-(trifluoromethoxy)phenyl]methyl}amino)-4-hydropyridino[2,3-b]pyrazin-4-yl]ethyl}acetamide;

N-(2-{2-(4-methoxyphenyl)-3-oxo-6-[(2-pyridylmethyl)amino]-4-hydropyridino[2,3-b]pyrazin-4-yl}ethyl)acetamide;

4-[2-(acetylamino)ethyl]-3-oxo-6-({[3-(trifluoromethyl)phenyl]methyl}amino)-4-hydropyridino[2,3-b]pyrazine-2-carboxylic acid;

N-{2-[6-({[2-fluoro-5-(trifluoromethyl)phenyl]methyl}amino)-2-(4-methoxyphenyl)-3-oxo-4-hydropyridino[2,3-b]pyrazin-4-yl]ethyl}acetamide;

(3R)-3-[2-(4-methoxyphenyl)-3-oxo-6-({[3-(trifluoromethyl)phenyl]methyl}amino)(4-hydropyridino[2,3-b]pyrazin-4-yl)]butanamide;

N-[2-(4-methoxyphenyl)-6-{[(5-methylisoxazol-3-yl)methyl]amino}-3-oxo-4-hydropyridino[2,3-b]pyrazin-4-yl)ethyl]acetamide;

N-{2-[2-[4-(2-methoxyethoxy)phenyl]-3-oxo-6-({[3-(trifluoromethyl)phenyl]methyl}amino)-4-hydropyridino[2,3-b]pyrazin-4-yl]-ethyl}acetamide;

N-{2-[3-oxo-2-(4-propylphenyl)-6-({[3-(trifluoromethyl)phenyl]methyl}amino)-4-hydropyridino[2,3-b]pyrazin-4-yl]ethyl}acetamide;

N-{2-[2-[4-(acetylamino)phenyl]-3-oxo-6-({[3-(trifluoromethyl)phenyl]methyl}amino)-4-hydropyridino[2,3-b]pyrazin-4-yl]ethyl}acetamide;

N-{2-[2-(4-methylphenyl)-3-oxo-6-({[3-(trifluoromethyl)phenyl]methyl}amino)-4-hydropyridino[2,3-b]pyrazin-4-yl]ethyl}acetamide;

N-{2-[2-(4-ethylphenyl)-3-oxo-6-({[3-(trifluoromethyl)phenyl]methyl}amino)-4-hydropyridino[2,3-b]pyrazin-4-yl]ethyl}acetamide;

N-{2-[2-(4-fluorophenyl)-3-oxo-6-({[3-(trifluoromethyl)phenyl]methyl}amino)-4-hydropyridino[2,3-b]pyrazin-4-yl]ethyl}acetamide;

3-[2-(4-methylphenyl)-3-oxo-6-({[3-(trifluoromethyl)phenyl]methyl}amino)-4-hydropyridino[2,3-b]pyrazin-4-yl]propanamide;

3-[2-(4-ethylphenyl)-3-oxo-6-({[3-(trifluoromethyl)phenyl]methyl}amino)-4-hydropyridino[2,3-b]pyrazin-4-yl]propanamide;

3-[2-[4-(2-methoxyethoxy)phenyl]-3-oxo-6-({[3-(trifluoromethyl)phenyl]methyl}amino)-4-hydropyridino[2,3-h]pyrazin-4-yl]propanamide;

3-[3-oxo-2-(4-propylphenyl)-6-({[3-(trifluoromethyl)phenyl]methyl}amino)-4-hydropyridino[2,3-b]pyrazin-4-yl]propanamide;

N-[2-(6-{[(3,4-dichlorophenyl)methyl]amino}-2-(4-methoxyphenyl)-3-oxo(4-hydropyridino[2,3-b]pyrazin-4-yl))ethyl]-2-(dimethylamino)acetamide;

{N-[2-(6-{[(3,4-dichlorophenyl)methyl]amino}-2-(4-methoxyphenyl)-3-oxo-4-hydropyridino[2,3-b]pyrazin-4-yl)ethyl]carbamoyl}methyl acetate;

N-[2-(6-{[(3,4-dichlorophenyl)methyl]amino}-2-(4-methoxyphenyl)-3-oxo(4-hydropyridino[2,3-b]pyrazin-4-yl))ethyl]-2-hydroxyacetamide;

4-[2-(4-methoxyphenyl)-3-oxo-6-({[3-(trifluoromethyl)phenyl]methyl}amino)-4-hydropyridino[2,3-b]pyrazin-4-yl]butanamide;

4-[2-methyl-3-oxo-6-({[3-(trifluoromethyl)phenyl]methyl}amino)-4-hydropyridino[2,3-b]pyrazin-4-yl]butanamide;

N-{2-[3-oxo-2-[4-(trifluoromethyl)phenyl]-6-({[3-(trifluoromethyl)phenyl]methyl}amino)-4-hydropyridino[2,3-b]pyrazin-4-yl]ethyl}acetamide;

3-[3-oxo-2-[4-(trifluoromethyl)phenyl]-6-({[3-(trifluoromethyl)phenyl]methyl}amino)-4-hydropyridino[2,3-b]pyrazin-4-yl]propanamide;

2-[2-(4-methoxyphenyl)-3-oxo-6-({[3-(trifluoromethyl)phenyl]methyl}amino)-4-hydropyridino[2,3-b]pyrazin-4-yl]acetamide;

(3S)-3-[2-(4-methoxyphenyl)-3-oxo-6-({[3-(trifluoromethyl)phenyl]methyl}amino)(4-hydropyridino[2,3-b]pyrazin-4-yl)]butanamide;

2-amino-N-[2-(6-{[(3,4-dichlorophenyl)methyl]amino}-2-(4-methoxyphenyl)-3-oxo(4-hydropyridino[2,3-b]pyrazin-4-yl))ethyl]acetamide;

2-(acetylamino)-N-[2-(6-{[(3,4-dichlorophenyl)methyl]amino}-2-(4-methoxyphenyl)-3-oxo(4-hydropyridino[2,3-b]pyrazin-4-yl))ethyl]acetamide;

N-{2-[3-oxo-2-propyl-6-({[3-(trifluoromethyl)phenyl]methyl}amino)-4-hydropyridino[2,3-b]pyrazin-4-yl]ethyl}acetamide;

N-{2-[2-ethyl-3-oxo-6-({[3-(trifluoromethyl)phenyl]methyl}amino)-4-hydropyridino[2,3-b]pyrazin-4-yl]ethyl}acetamide;

3-(6-{[(3,4-dichlorophenyl)methyl]amino}-2-(4-methoxyphenyl)-3-oxo(4-hydropyridino[2,3-b]pyrazin-4-yl))-N-(2-hydroxyethyl)propanamide;

N-{2-[3-oxo-2-(2-phenylethyl)-6-({[3-(trifluoromethyl)phenyl]methyl}amino)-4-hydropyridino[2,3-b]pyrazin-4-yl]ethyl}acetamide;

N-[2-(6-{[(3,4-dichlorophenyl)methyl]amino}-2-[4-(methylsulfonyl)phenyl]-3-oxo-4-hydropyridino[2,3-b]pyrazin-4-yl)ethyl]acetamide;

4-((3S)-6-oxo(3-piperidyl))-2-(4-methoxyphenyl)-6-({[3-(trifluoromethyl)phenyl]methyl}amino)-4-hydropyridino[3,2-b]pyrazin-3-one;

N-(2-{6-[(2-methoxyethyl)amino]-2-(4-methoxyphenyl)-3-oxo-4-hydropyridino[2,3-b]pyrazin-4-yl}ethyl)acetamide;

N-[2-(2-(3,4-dichlorophenyl)-6-{[(3,4-dichlorophenyl)methyl]amino}-3-oxo-4-hydropyridino[2,3-b]pyrazin-4-yl)ethyl]acetamide;

N-[2-(6-{[3-(2,5-dichlorophenoxy)propyl]amino}-2-(4-methoxyphenyl)-3-oxo-4-hydropyridino[2,3-b]pyrazin-4-yl)ethyl]acetamide;

{N-[2-(4-methoxyphenyl)-3-oxo-6-({[3-(trifluoromethyl)phenyl]methyl}amino)-4-hydropyridino[2,3-b]pyrazin-4-yl]carbamoyl}methyl acetate;

N-[2-(7-{[(3,4-dichlorophenyl)methyl]amino}-2-oxo-3-(3-pyridyl)hydropyridino[3,4-b]pyrazinyl)ethyl]acetamide;

CVT-012258    N-[2-(7-{[(3,4-dichlorophenyl)methyl]amino}-3-(4-methylphenyl)-2-oxohydropyridino[3,4-b]pyrazinyl)ethyl]acetamide;

N-[2-(7-{[(3,4-dichlorophenyl)methyl]amino}-3-(4-methoxyphenyl)-2-oxohydropyridino[3,4-b]pyrazinyl)ethyl]acetamide;

N-[2-(7-[(3,4-dichlorophenyl)methyl]amino}-3-(4-chlorophenyl)-2-oxohydropyridino[3,4-b]pyrazinyl)ethyl]acetamide;

N-[2-(7-{[(3,4-dichlorophenyl)methyl]amino}-3-methyl-2-oxohydropyridino[3,4-b]pyrazinyl)ethyl]acetamide;

N-[2-(7-{[(3,4-dichlorophenyl)methyl]amino}-3-(4-methoxyphenyl)-2-oxohydroquinoxalinyl)ethyl]acetamide;

N-{2-[3-(4-methoxyphenyl)-2-oxo-7-({[3-(trifluoroethyl)phenyl]methyl}amino)hydroquinoxalinyl]ethyl}acetamide;

N-{2-[2-oxo-3-(3-pyridyl)-7-({[3-(trifluoromethyl)phenyl]methyl}amino)hydroquinoxalinyl]ethyl}acetamide;

N-{2-[3-(4-methylphenyl)-2-oxo-7-({[3-(trifluoromethyl)phenyl]methyl}-amino)hydroquinoxalinyl]ethyl}acetamide;

N-{2-[3-[4-(2-methoxyethoxy)phenyl]-2-oxo-7-({[3-(trifluoromethyl)phenyl]methyl}amino)hydroquinoxalinyl]ethyl}acetamide;

N-{2-[3-methyl-2-oxo-7-({[3-(trifluoromethyl)phenyl]methyl}-amino)hydroquinoxalinyl]ethyl}acetamide;

(N-{2-[3-methyl-2-oxo-7-({[3-(trifluoromethyl)phenyl]methyl}amino)hydroquinoxalinyl]ethyl}carbamoyl)methyl acetate;

2-hydroxy-N-{2-[3-methyl-2-oxo-7-{[3-(trifluoromethyl)phenyl]methyl}amino)hydroquinoxalinyl]ethyl}acetamide;

N-{2-[3-(4-ethylphenyl)-2-oxo-7-({[3-(trifluoromethyl)phenyl]methyl}amino)hydroquinoxalinyl]ethyl}acetamide;

N-(2-{3-(3,4-dichlorophenyl)-2-oxo-7-[phenylmethoxy)carbonylamino]hydroquinoxalinyl}ethyl)acetamide; and N-(2-{3-(4-methoxyphenyl)-2-oxo-7-[phenylmethoxy)carbonylamino]hydroquinoxalinyl}-ethyl)acetamide.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or
3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1-10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "lower alkylene" refers to a diradical of a branched or unbranched saturated hydrocarbon chain, preferably having from 1, 2, 3, 4, 5, or 6 carbon atoms.

The term "substituted alkylene" refers to:
(1) an alkylene group as defined above having 1, 2, 3, 4 or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH═CH$_2$), 1-propylene or ally (—CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or prop-1-yn-3-yl, —CH$_2$≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, aryloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]hept-2-yl, (2,3,3 trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, acyloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-oxide and N-alkoxy derivatives of nitrogen containing heteroaryl compounds, for example pyridine-N-oxide derivatives.

The term "heteroarylene" refers to a diradical of a heteroaryl group as defined above. This term is exemplified by groups such as 2,5-imidazolene, 3,5-[1,2,4]oxadiazolene, 2,4-oxazolene, 1,4-pyrazolene, and the like. For example, 1,4-pyrazolene is:

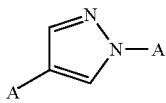

where A represents the point of attachment.

Unless otherwise constrained by the definition for the heteroaryl or heteroarylene substituent, such heteroaryl or hetararylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

nocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclic substituent, such heterocyclic groups can be optionally substituted with 1,2,3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$ alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—.

The term "thiocarbonyl" refers to a group —C(S)—.

The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

"Parenteral administration" is the systemic delivery of the therapeutic agent via injection to the patient.

The term "therapeutically effective amount" refers to that amount of a compound of Formula I that is sufficient to effect treatment, as defined below, when administered to a mammal in need of such treatment. The therapeutically effective amount will vary depending upon the specific activity of the therapeutic agent being used, and the age, physical condition, existence of other disease states, and nutritional status of the patient. Additionally, other medication the patient may be receiving will effect the determination of the therapeutically effective amount of the therapeutic agent to administer.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, rnatonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, "pharmaceutically acceptable carrier" includes any and all solvents, dispersion media, solubilizers, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is 2-(acetylamino)ethyl, $R^2$ is 3,4-dichlorobenzyl, and $R^3$ is 4-methoxyphenyl,

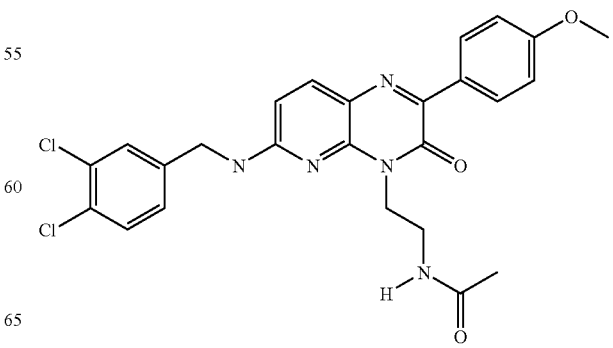

which is named:

N [2-(6-{[(3,4-dichlorophenyl)methyl]amino}-2-(4-methoxyphenyl)-3-oxo-4-hydropyridirio[2,3-b]pyrazin-4-yl)ethyl]acetamide.

Pharmaceutical Compositions

When selected as the SCD inhibitor, the compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula

One preferred method of preparing compounds of Formula I is shown in Reaction Scheme I.

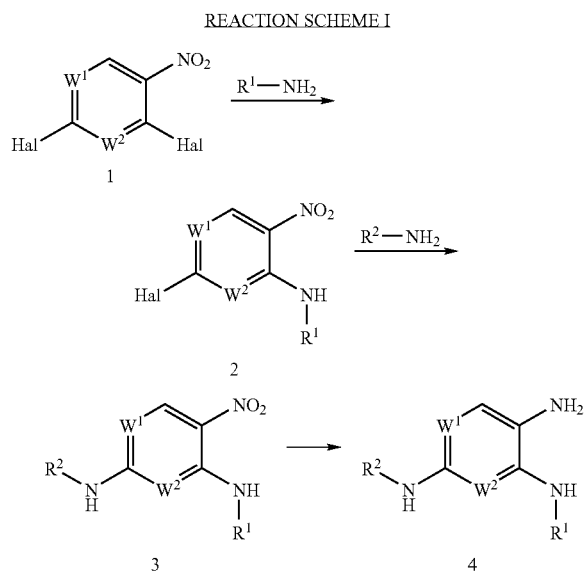

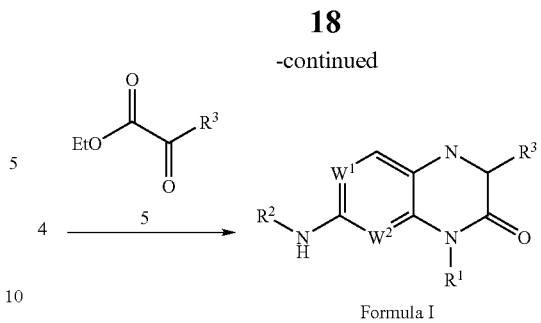

Step 1—Preparation of Formula (2)

The compound of formula (2) is made by replacing the halogen group adjacent to the nitro moiety on the commercially available formula (1) compound (i.e., 2,6-dichloro-3-nitropyridine, 2,4-difloro-5-nitropyridine, 2,4-dichloro-nitrobenzene, or the like) with a compound of formula $R^1NH$, in the presence of a base. The reaction is carried out in a dipolar aprotic solvent such as tetrahydrofuran (THF), acetone, or ethylacetate, and the like, at a temperature of around $-60°$ C. to around $-90°$ C., for about 30 minutes to an hour. The reaction mixture is then allowed to warm to room temperature with continued stirring, approximately 2 to 5 hours. When the reaction is substantially complete, the product of formula (2) is isolated by conventional means, for example by removal of the solvent under reduced pressure, followed by chromatography of the residue on silica gel. Alternatively, the compound of formula (2) is used in the next step without purification.

Step 2—Preparation of Formula (3)

The compound of formula (3) is made by replacing the remaining chloro group on the compound of formula (2) with a compound of formula $R^2NH_2$ in the presence of a base. A similar procedure is used as described with respect to step 2, however, the reaction is conducted at a temperature of approximately $50°$ C. to approximately $80°$ C. for 12 to 24 hours. When the reaction is substantially complete, the product of formula (3) may by isolated conventional means but is typically used in the next step without purification.

Step 3—Preparation of Formula (4)

The formula (3) nitro compound is then reduced to the corresponding amine analog, compound (4), via conventional reduction techniques. Suitable methods include, but are not limited to, reaction with $Na_2S_2O_4$ and $Na_2CO_3$ at a temperature ranging from $50°$ C. to $80°$ C. for 5 to 12 hours. After the reaction is allowed to cool to room temperature the product may be extracted by dilution with EtOAc followed by washing with saturated. $NaHCO_4$ solution and brine. The combined organic phase can then be dried over $MgSO_4$ and concentrated to provide the compound of formula (4) in crude form which can be used in the next step without further purification.

Alternatively, the nitro group can be reduced by reaction with hydrazine and a Raney-Nickel catalyst. In this method, the nitro compound is placed in a methanol solution to which the hydrazine is added. Then the reaction mixture is heated to approximately $50°$ C. to $80°$ C. and the Raney-Nickel catalyst gently added to insure even and steady evolution of the nitrogen gas. The reaction proceeds for approximately 1 hour whereupon the reaction mixture is allowed to cool to room temperature, the catalyst filtered off, and the filter cake washed with methanol. The resulting solution may be concentrated and purified using conventional methods, i.e., chromatography using a methanol/dichloromethane gradient to provide the desired amine.

Step) 4—Preparation of Formula I

The final step in the synthesis involves the formation of the pyrimidine ring and the addition of the $R^3$ substituent. This is achieved by reacting the amino compound of formula (4) with an ethyl oxoacete derivative having the desired $R^3$ moiety, i.e., a compound of formula (5). The compound of formula (4) is dissolved in 2% v/v AcOH in EtOH and then the compound of formula (5) is added. The reaction is stirred at 60° C. to 90° C. for 12 to 24 hours. The resulting suspension is cooled to room temperature and the final product extracted by the addition of a polar solvent such as methanol followed by filtration and washing with additional polar solvent. The compound of Formula I can then be dried under vacuum to remove any remaining solvent.

Alternatively, the pyrimidine ring can be formed by first dissolving the amino compound of formula (4) into acetonitrile followed the by addition a catalytic drop of acid, such as glacial acetic acid. The oxoacete derivative is then added and the mixture heated for approximately 20 to 40 minutes in a microwave at 120° C. The reaction mixture may them be filtered, concentrated, and purified using column chromatography eluting with MeOH/dichloromethane gradient to provide the compound of Formula I.

Alternative Preparation —$R^1$ is a Nitrogen-Containing Heterocycle

Compounds of Formula I wherein $R^1$ is a nitrogen-containing heterocycle may be prepared as described above with the additional requirement that the nitrogen atom in the $R^1$ heterocycle be protected by a suitable protecting group such as an N-tert-butoxycarbonyl group. If desired the protecting group may be removed after Step 4 using conventional techniques, i.e., heating at 60° C. to 80° C. in a mixture of acetonitrile and hydrochloric acid. The acidic mixture is neutralized after cooling with an aqueous base such as KOH and the product extracted using dichloromethane.

Alternative Preparation—Secondary Modification of $R^1$

It will be appreciated that secondary modification may be made to the $R^1$ moiety after the compound of Formula I has been made. As was discussed in the $R^1$ heterocycles, this type of modification generally will involve the use of a protected terminal $R^1$ amino group. One the protecting group is removed, the terminal $R^1$ amino group may be modified my reaction with any number of reactant allowing for the addition of a desired $R^5$ or $R^7$ substituent.

In one type of secondary modification, the deprotected compound of Formula I is dissolved in the appropriate non-protic solvent, i.e., acetonitrile or the like, and then an acidic version of the desired $R^5$ substituent, $R^6$—C(O)—OH, is added to the reaction mixture followed by 2-(1H-benzotriazol-1-yl)-1,1,3,3-tetramethyl-aronium tetrafluoroborate (TBTU) and diisopropylethyleneamine. After briefly heating to approximately 50° to 70° C., the reaction mixture is cooled to room temperature and the precipitated end product filtered off and washed with additional solvent to provide the final product of Formula I.

In another example of secondary modification, after the deprotected compound of Formula I is dissolved in the appropriate non-protic solvent, i.e., acetonitrile, it is placed in a microwave vessel with methyl formate and heated at 135° C. to 150° C. for 15 to 30 minutes. Cooling and filtration will provide the desired end product.

In still another example of secondary modification, the deprotected compound of Formula I is dissolved in acetonitrile and dichloromethane. A base such as diisopropylethyleneamine is then added along with {1H}-pyrazole-1-hydroxamidine hydrochloride. The reaction is heated at 30° C. to 50° C. for 15 to 30 minutes. Cooling and filtration will provide a compound of Formula I where in $R^4$ is —C(NH)NH$_2$.

Utility Testing and Administration

The present invention relates to compounds, pharmaceutical compositions and methods of using the compounds and pharmaceutical compositions for the treatment and/or prevention of diseases mediated by SCD. The methods and pharmaceutical compositions are particularly suitable for use in the treatment of diseases related to dyslipidemia and disorders of lipid metabolism, especially diseases related to elevated plasma and tissue lipid levels, such as cardiovascular disease, diabetes, obesity, metabolic syndrome, fatty liver diseases and the like.

In general, the compounds of the invention find utility in the treatment of a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels or hepatic or peripheral tissue lipid accumulation), especially levels higher than normal, preferably where said lipid is a fatty acid, such as a free or complexed fatty acid, triglycerides, phospholipids, cholesterol or cholesteryl ester such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound inhibits the activity of SCD.

The general value of the compounds of the invention in inhibiting the activity of SCD can be determined using the assay described below in Example 14. Additionally, the general value of the compounds in treating disorders and diseases may be established in industry standard animal models for demonstrating the efficacy of compounds in treating obesity, diabetes or abnormal triglyceride or cholesterol levels or for improving glucose tolerance.

Utility

The compounds of the instant invention are inhibitors of SCD and are useful for treating diseases and disorders in humans and other organisms, including all those human diseases and disorders which are the result of aberrant SCD biological activity or which may be ameliorated by inhibition of SCD biological activity.

As defined herein, an SCD-mediated disease or condition includes but is not limited to a disease or condition which is, or is related to, cardiovascular disease, dyslipidemias, fatty liver diseases, coronary artery disease, atherosclerosis, heart disease, cerebrovascular disease (including, but not limited, to stroke, ischemic stroke and transient ischemic attack (TIA), peripheral vascular disease, ischemic retinopathy, cancer and skin conditions.

Dyslipidemia, as used herein, includes, but is not limited to, disorders related to the serum and tissue levels of triglycerides, i.e., hypertriglyceridemia, fatty liver diseases LDL, VLDL, and/or HDL, cholesterol, and total cholesterol. Dyslipidemia also includes disorders related to the Δ9 fatty acid Desaturation Indexes (e.g. the ratio of 18:1/18:0 fatty acids. Disorders of polyunsaturated fatty acid metabolism (PUPA) are also included as are cholesterol disorders such as familial combined hyperlipidemia and those disorders involving defective reverse cholesterol transport.

SCD-mediated diseases or conditions relating to hypertriglyceridemia, include but are not limited to, hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

Metabolic syndrome, Syndrome X and Pre-Diabetes are also within the scope of the term "SCD-mediated disease" including all of the various component condition that make up the syndromes such as, but not limited to, dyslipidemia, obesity, insulin resistance, hyperinsulenemia, decreased glucose tolerance, hypertension, microalbuminemia, hyperuricaemia, and hypercoagulability, diabetes, non-insulin-dependent diabetes mellitus, Type I diabetes, Type II diabetes, diabetic complications, body weight disorders such as overweight, cachexia and anorexia, and body mass index and leptin related diseases.

As used herein, the term "metabolic syndrome" is a recognized clinical term used to describe a condition comprising combinations of Type II diabetes, impaired glucose tolerance, insulin resistance, hyperinsulinemia, hypertension, obesity, increased abdominal girth, hypertriglyceridemia, low HDL, hyperuricaemia, hypercoagulability and/or microalbuminemia.

An SCD-mediated disease or condition also includes various hepatic conditions such as hepatitis, hepatic steatosis, hepatic fibrosis, hepatic cirrhosis, non-alcoholic hepatitis, non-alcoholic steatohepatitis (NASH), alcoholic hepatitis, fatty liver, non-alcoholic fatty liver disease (NAFLD), acute fatty liver, fatty liver of pregnancy, drug-induced hepatitis, erythrohepatic protoporphyria, iron overload disorders, hereditary hemochromatosis, hepatoma and conditions related thereto.

Various skin and mucosal tissue disorders fall within the scope of an SCD-mediated disease or condition including, but not limited to, eczema, acne, psoriasis, keloid scar formation or prevention, diseases related to production or secretions from mucous membranes, such as monounsaturated fatty acids, wax esters, and the like. Inflammation, sinusitis, asthma, pancreatitis, osteoarthritis, rheumatoid arthritis, cystic fibrosis, and pre-menstrual syndrome may also be considered SCD-mediated diseases or conditions as may diseases or conditions which is, or is related to cancer, neoplasia, malignancy, metastases, tumors (benign or malignant), carcinogenesis, hepatomas and the like. SCD-mediated diseases or conditions also include diseases or conditions which are, or are related to, neurological diseases, psychiatric disorders, multiple sclerosis, eye diseases, and immune disorders. An SCD-mediated disease or condition also includes a disease or condition which is, or is related to, viral diseases or infections.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

Testing

The identification of compounds of the invention as SCD inhibitors was readily accomplished using the SCD enzyme and microsomal assay procedure described in Talarno and Bloch (1969) *Analytical Biochemistry* 29:300-304. When tested in this assay, compounds of the invention had less than 50% remaining SCD activity at 10 µM concentration of the test compound, preferably less than 40% remaining SCD activity at 10 µM concentration of the test compound, more preferably less than 30% remaining SCD activity at 10 µM concentration of the test compound, and even more preferably less than 20% remaining SCD activity at 10 µM concentration of the test compound, thereby demonstrating that the compounds of the invention are potent inhibitors of SCD activity.

Other methods of testing the compounds disclosed herein are also readily available to those skilled in the art. Thus, in addition, said contacting may be accomplished in vivo. In one such embodiment, said contacting in step (a) is accomplished by administering said chemical agent to an animal afflicted with a Fatty acid, triglyceride (TG)- or very low density lipoprotein (VLDL)-related disorder and subsequently detecting a change in plasma or tissue triglyceride level or fatty acid composition in said animal thereby identifying a therapeutic agent useful in treating a dyslipidemia or disorder of lipoprotein metabolism. In such embodiment, the animal may be a human, such as a human patient afflicted with such a disorder and in need of treatment of said disorder.

In specific embodiments of such in vivo processes, said change in SCD activity in said animal is a decrease in activity, preferably wherein said SCD modulating agent does not substantially inhibit the biological activity of a Δ5 desaturase, Δ6 desaturase, or fatty acid synthetase.

The model systems useful for compound evaluation may include, but not limited to, the use of liver microsomes, such as from mice that have been maintained on a high carbohydrate or high-fate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate or high fat diet to increase SCD activity in microsomes and/or to elevate plasma and/or tissue triglyceride levels or Δ9 fatty acid desaturation indexes (i.e., the 18:1 n-9/18:0. 16:1 n-7/16 ratio); alternatively mice on a normal diet or mice with normal triglyceride levels may be used. Mouse models having hypertriglyceridemia due to genetic or naturally occurring mutations are also available as is the mouse phenome database. Rabbits, hamsters and monkeys are also useful as animal models, especially those expressing CETP (cholesteryl ester transfer protein).

Another suitable method for determining the in vivo efficacy of the compounds of the invention is to indirectly measure their impact on inhibition of SCD enzyme by measuring a subject's Δ9 Desaturation Index after administration of the compound. "Desaturation Index" as employed in this specification means the ratio of the product over the substrate for the SCD enzyme as measured from a given tissue or plasma sample. This may be calculated using three different equations 18:1n-9/18:0 (oleic acid over stearic acid); 16:1n-7/16:0 (palmitoleic acid over palmitic acid); and/or 16:1n-7+18:1n-7/16:0 (measuring all reaction products of 16:0 desaturation over 16:0 substrate). SCD activity may also be monitored in a given tissue or plasma sample by determining the fatty acid composition by HPLC, GC or TL and determining whether there are changes in the mass or molar percentage composition of SCD product fatty acids.

Administration

The compounds of Formula I may be administered in either single or multiple doses by any of the accepted modes of administration of agents having similar utilities, for example as described in those patents and patent applications incorporated by reference, including buccal, intranasal, intra-arterial injection, intravenously, intraperitoneally, parenterally, intramuscularly, subcutaneously, orally, topically, or as an inhalant.

Oral administration is the preferred route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345.

In a other embodiments, the compounds of the invention are incorporated into a pharmaceutical formulation containing a pharmaceutically acceptable carrier that is generally suited to topical drug administration and comprising any such material known in the art. Suitable carriers are well known to those of skill in the art and the selection of the carrier will depend upon the form of the intended pharmaceutical formulation, e.g., as an ointment, lotion, cream, foam, microemulsion, gel, oil, solution, spray, salve, or the like, and may be comprised of either naturally occurring or synthetic materials. It is understood that the selected carrier should not adversely affect the compound of Formula I other components of the pharmaceutical formulation.

Suitable carriers for these types of formulations include, but are not limited to, vehicles including Shephard's™ Cream, Aquaphor™, and Cetaphil™ lotion. Other preferred carriers include ointment bases, e.g., polyethylene glycol-1000 (PEG-1000), conventional creams such as HEB cream, gels, as well as petroleum jelly and the like. Examples of suitable carriers for use herein include water, alcohols and other nontoxic organic solvents, glycerin, mineral oil, silicone, petroleum jelly, lanolin, fatty acids, vegetable oils, parabens, waxes, and the like. Particularly preferred formulations herein are colorless, odorless ointments, lotions, creams, microemulsions and gels.

Ointments are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's Pharmaceutical Sciences, $20^{th}$ Ed. (Easton, Pa.: Mack Publishing Company, 2000), ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols (PEGs) of varying molecular weight; again, reference may be had to Remington's, supra, for further information.

Lotions are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. A particularly preferred lotion formulation for use in conjunction with the present invention contains propylene glycol mixed with a hydrophilic petrolatum such as that which may be obtained under the trademark Aquaphor™ from Beiersdorf, Inc. (Norwalk, Conn.).

Creams containing the active agent are, as known in the art, viscous liquid or semisolid emulsions, either oil-in-water or water-in-oil. Cream bases are water-washable, and contain an oil phase, an emulsifier, and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic, or amphoteric surfactant.

Microemulsions are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, a surfactant (emulsifier), a co-surfactant (co-emulsifier), an oil phase, and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives, and fatty alcohols. Preferred emulsifier/co-emulsifier combinations are generally although not necessarily selected from the group consisting of glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Gel formulations are semisolid systems consisting of either small inorganic particle suspensions (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in the topical formulations of the invention. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients, and preservatives.

Examples of solubilizers include, but are not limited to, the following: hydrophilic ethers such as diethylene glycol monoethyl ether (ethoxydiglycol, available commercially as Transcutol™) and diethylene glycol monoethyl ether oleate (available commercially as Softcutor™); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol™); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in the formulation, e.g., anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In the preferred topical formulations of the invention, the active agent is present in an amount in the range of approximately 0.25 wt. % to 75 wt. % of the fog ululation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Also, the pharmaceutical formulation may be sterilized or mixed with auxiliary agents, e.g., preservatives, stabilizers, wetting agents, buffers, or salts for influencing osmotic pressure and the like. Sterile injectable solutions are prepared by incorporating the compound of Formula I or Formula II in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

SCD inhibitors such as the compounds of Formula I are effective over a wide dosage range and is generally administered in a pharmaceutically effective amount. Typically, for oral administration, each dosage unit contains from 1 mg to 2 g of an SCD inhibitor, more commonly from 1 to 700 mg, and for parenteral administration, from 1 to 700 mg of a stearoyl-CoA desaturase inhibitor, more commonly about 2 to 200 mg. It will be understood, however, that the amount of the SCD inhibitor actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage foiins such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

A. Preparation of a Compound of Formula (2) in which $W^1$ is CH, $W^2$ is N, $R^1$ is —$CH_2CH_2NHC(O)CH_3$

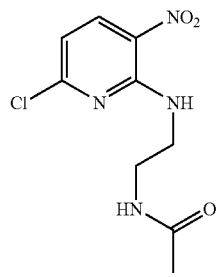

To a solution of 3.0 g (15.5 mmol) 2,6-dichloro-3-nitropyridine in 50 mL of THF at −78° C. under Ar atmosphere was added 2.7 mL (15.5 mmol) of N,N-diisopropylethyl amine followed by 1.6 mL (15.5 mmol) of N-acetylethylenediamine. The mixture was stirred at −78° C. for 30 min, allowed to warm to room temperature, and stirred for 72 hours. The solvent was removed in vacuo and the residue was purified by flash chromatography eluting with MeOH/dichloromethane gradient (1→10%) to provide N-(2-(6-chloro-3-nitropyridin-2-ylamino)ethyl)acetamide as pale yellow solid.

B. Preparation of Compounds of Formula (2) varying $R^1$

Similarly, following the procedure of Example 1A above, but optionally substituting other compounds of formula (1) for 2,6-dichloro-3-nitropyridine, and optionally substituting other amines of formula $R^1NH_2$ for acetylethylenediamine, the following compound of formula (2) was prepared: (tert-butoxy)-N-{2-[(6-chloro-3-nitro(2-pyridyl))amino] ethyl}carboxamide.

C. Preparation of Compounds of Formula (2) varying $R^1$

Similarly, following the procedure of Example 2A above, but optionally substituting other compounds of formula (1) for 2,6-dichloro-3-nitropyridine, and optionally substituting other amines of formula $R^1NH_2$ for acetylethylenediamine, other compounds of formula (2) are prepared.

EXAMPLE 2

Preparation of a Compound of Formula (3)

A. Preparation of a Compound of Formula in which $W^1$ is CH, $W^2$ is N, $R^1$ is —$CH_2CH_2NHC(O)OC(CH_3)_3$, and $R^2$ is 3,4-Dichlorophenyl

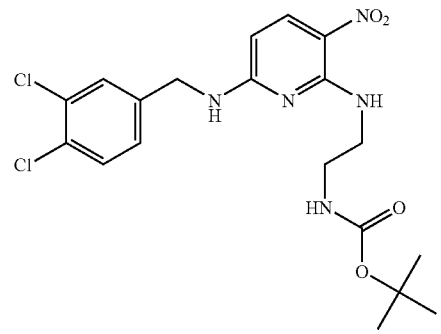

900 mg of (tert-butoxy)-N-{2-[(6-chloro-3-nitro(2-pyridyl))amino]ethyl}carboxamide, as prepared in Example 1, was combined with 990 μL of N,N-diisopropylethylamine and 760 μL of 3,4-dichlorobenzylamine in 10 mL of THF. The mixture was stirred at 90° C. for 16 h. Significant precipitate had formed. The solution was concentrated down to form a yellow residue which was resuspended in MeOH. N-{2-[(6-{[(3,4-dichlorophenyl)methyl]amino}-3-nitro(2-pyridyl)) amino]ethyl}(tert-butoxy)carboxamide was filtered out as yellow precipitate. The product was used in the next step without further purification.

B. Preparation of Compounds of Formula (3) varying $R^1$ and $R^2$

Similarly, following the procedure of Example 2A above, but optionally substituting other compounds of formula (2) for (tert-butoxy)-N-{2-[(6-chloro-3-nitro(2-pyridyl))amino] ethyl}carboxamide, and optionally substituting other amines of formula $R^2NR$, for 3,4-dichlorobenzylamine, the following compounds of formula (3) were prepared:

N-2-[(6-{[(3,4-dichlorophenyl)methyl]amino}-3-nitro-2-pyridyl)amino]ethyl acetamide;

N-{2-[(6-{[(4-fluorophenyl)methyl]amino}-3-nitro-2-pyridyl)amino]ethyl}acetamide;

N-{2-[(6-{[(3-chlorophenyl)methyl]amino}-3-nitro-2-pyridyl)amino]ethyl}acetamide;

N-{2-[(6-[(3-chloro-4-fluorophenyl)methyl]amino-3-nitro-2-pyridyl)amino]ethyl}acetamide;

3-[(6-{[(3,4-dichlorophenyl)methyl]amino}-3-nitro-2-pyridyl)amino]propanamide;

N-(2-{[3-nitro-6-({[3-(trifluoromethyl)phenyl] methyl}amino)-2-pyridyl]amino}ethyl)acetamide;

N-(2-{[3-nitro-6-({[4-(trifluoromethyl)phenyl] methyl}amino)-2-pyridyl]amino}ethyl)acetamide;

{6-[((3S)pyrrolidin-3-yl)amino]-5-nitro(2-pyridyl)}[(3,4-dichlorophenyl)methyl]amine;

ethyl 4-[(6-{[(3,4-dichlorophenyl)methyl]amino}-3-nitro-2-pyridyl)amino]butanoate;

3 4-[(6-{[(3,4-dichlorophenyl)methyl]amino}-3-nitro-2-pyridyl)amino]butanoic acid;

ethyl 3-[(6-{[(3,4-dichlorophenyl)methyl]amino}-3-nitro-2-pyridyl)amino]propanoate;

3-[(6-{[(3,4-dichlorophenyl)methyl]amino}-3-nitro-2-pyridyl)amino]propanoic acid;

N-{2-[(6-{[(3-bromophenyl)methyl]amino}-3-nitro-2-pyridyl)amino]ethyl}acetamide;

N-(2-{[6-({[3,5-bis(trifluoromethyl)phenyl]methyl}amino)-3-nitro-2-pyridyl]amino}ethyl)acetamide;

N-(2-{[6-({[4-fluoro-3-(trifluoromethyl)phenyl] methyl}amino)-3-nitro-2-pyridyl]amino}ethyl)acetamide;

N-(2-{[3-nitro-6-({[6-(trifluoromethyl)(2-pyridyl)] methyl}amino)-2-pyridyl]amino}ethyl)acetamide;

N-(2-{[3-nitro-6-([5-(trifluoromethyl)(3-pyridyl)] methyl}amino)-2-pyridyl]amino 1 ethyl)acetamide; and 2-{[3-nitro-6-({[3-(trifluoromethyl)phenyl]methyl}amino)-2-pyridyl]amino}ethan-1-ol;

C. Preparation of Compounds of Formula (3) varying $R^1$ and $R^2$

Similarly, following the procedure of Example 2A above, but optionally substituting other compounds of formula (2) for (tert-butoxy)-N-{2-[(2-chloro-5-nitropyrimidin-4-yl)amino]ethyl}-carboxamide, and optionally substituting other amines of formula $R^2NH_2$ for 3,4-dichlorobenzylamine, other compounds of formula (3) are prepared.

EXAMPLE 3

Preparation of a Compound of Formula I

A. Preparation of a Compound of Formula I in which $W^1$ is CH, $W^2$ is N, $R^1$ is —$CH_2CH_2NHC(O)CH_3$, $R^2$ is 3,4-Dichlorophenyl, and $R^3$ is 4-Methoxyphenyl

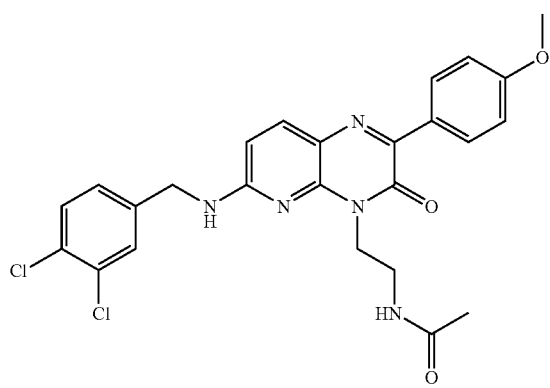

N-(2-(6-(3,4-dichlorobenzylamino)-3-nitropyridin-2-ylamino)ethyl)acetamide, as prepared in Example 2, was dissolved in 70 mL of 1:1 mixture of dioxane and water and 1.7 g of $Na_2S_2O_4$ (85% tech. grade, 2.9 mmol) and 1.1 g of $Na_2CO_3$ (8.5 mmol) were added. The mixture was stirred at room temperature for 10 min under the blanket of nitrogen, diluted with 50 mL of water, and extracted 3 times with 20 mL portions of EtOAc. Combined organic layers were washed with 20 mL of brine and concentrated. The residue was dissolved in 20 mL of 2% v/v AcOH in EtOH containing 130 mg (1.2 mmol) of ethyl 2-(4-methoxyphenyl)-2-oxoacetate. The reaction mixture was stirred at 80° C. for 6 h. The resulting suspension was concentrated down and subjected to chromatography eluting with 5% MeOH in dichloromethane. N-[2-(6-{[(3,4-dichlorophenyl)methyl]amino}-2-(4-methoxyphenyl)-3-oxo-4-hydropyridino[2,3-b]pyrazin-4-yl)ethyl]acetamide was obtained as a yellow solid.

$^1$H NMR ($\delta$, 400 MHz, CDCl$_3$) 8.27 (d, 2H); 7.90 (d, 1H); 7.48 (m, 1H); 7.43 (d, 1H); 7.23 (dd, 1H); 6.98 (d, 2H); 6.48 (d, 1H); 6.20 (bs, 1H); 5.44 (t, 1H); 4.66 (d, 2H); 4.59 (t, 2H); 3.87 (s, 3H); 3.65 (q, 2H); 1.90 (s, 3H).

B. Preparation of Compounds of Formula I varying $R^1$, $R^2$, and $R^3$

Similarly, following the procedure of Example 3A above, but optionally substituting other compounds of formula (3) for N-(2-(6-(3,4-dichlorobenzylamino)-3-nitropyridin-2-ylamino)ethyl)acetamide, and optionally substituting other oxoacetate of formula (5) for ethyl 2-(4-methoxyphenyl)-2-oxoacetate, the following compounds of Formula I were prepared:

N-[2-(6-{[(3,4-dichlorophenyl)methyl]amino}-2-(4-methoxyphenyl)-3-oxo(4-hydropyridino[2,3-b]pyrazin-4-yl)) ethyl](tert-butoxy)carboxamide;

N-[2-(6-{[(3,4-dichlorophenyl)methyl]amino}-2-(4-methoxyphenyl)-3-oxo-4-hydropyridino[2,3-b]pyrazin-4-yl) ethyl]acetamide;

N-[2-(6-{[(4-fluorophenyl)methyl]amino}-2-(4-methoxyphenyl)-3-oxo-4-hydropyridino[2,3-b]pyrazin-4-yl) ethyl]acetamide;

N-[2-(6-{[(3-chlorophenyl)methyl]amino}-2-(4-methoxyphenyl)-3-oxo-4-hydropyridino[2,3-b]pyrazin-4-yl) ethyl]acetamide;

N-[2-(6-{[(3-chloro-4-fluorophenyl)methyl]amino}-2-(4-methoxyphenyl)-3-oxo-4-hydropyridino[2,3-b]pyrazin-4-yl)ethyl]acetamide;

N-{2-[2-(4-methoxyphenyl)-3-oxo-6-({[3-(trifluoromethyl) phenyl]methyl}amino)-4-hydropyridino[2,3-b]pyrazin-4-yl]ethyl}acetamide;

N-{2-[2-(4-methoxyphenyl)-3-oxo-6-({[4-(trifluoromethyl) phenyl]methyl}amino)-4-hydropyridino[2,3-b]pyrazin-4-yl]ethyl}acetamide;

N-[2-(6-{[(3,4-dichlorophenyl)methyl]amino}-2-(4-methylthiophenyl)-3-oxo-4-hydropyridino[2,3-b]pyrazin-4-yl) ethyl]acetamide;

N-[2-(6-{[(3,4-dichlorophenyl)methyl]amino}-2-(4-methylphenyl)-3-oxo-4-hydropyridino[2,3-b]pyrazin-4-yl) ethyl]acetamide;

N-[2-(6-{[(3-bromophenyl)methyl]amino}-2-(4-methoxyphenyl)-3-oxo-4-hydropyridino[2,3-b]pyrazin-4-yl) ethyl]acetamide;

N-{2-[6-({[3,5-bis(trifluoromethyl)phenyl]methyl}amino)-2-(4-methoxyphenyl)-3-oxo-4-hydropyridino[2,3-b] pyrazin-4-yl]ethyl}acetamide;

N-{2-[6-({[4-fluoro-3-(trifluoromethyl)phenyl] methyl}amino)-2-(4-methoxyphenyl)-3-oxo-4-hydropyridino[2,3-b]pyrazin-4-yl]ethyl}acetamide;

N-{2-[2-(4-methoxyphenyl)-3-oxo-6-({[5-(trifluoromethyl) (3-pyridyl)]methyl}amino)-4-hydropyridino[2,3-b] pyrazin-4-yl]ethyl}acetamide;

N-(2-{2-(4-methoxyphenyl)-3-oxo-6-[benzylamino]-4-hydropyridino[2,3-b]pyrazin-4-yl}ethyl)acetamide;

N-(2-{2-(4-methoxyphenyl)-3-oxo-6-[(3-pyridylmethyl)amino]-4-hydropyridino[2,3-b]pyrazin-4-yl}ethyl)acetamide;

N-{2-(6-{[(3,4-dichlorophenyl)methyl]amino}-3-oxo-2-(3-pyridyl)-4-hydropyridino[2,3-b]pyrazin-4-yl)ethyl}acetamide;

N-[2-(6-{[(3-chloro-4-fluorophenyl)methyl]amino}-3-oxo-2-(3-pyridyl)-4-hydropyridino[2,3-b]pyrazin-4-yl)ethyl]acetamide;

N-{2-[3-oxo-2-(3-pyridyl)-6-({[3-(trifluoromethyl)phenyl]methyl}amino)-4-hydropyridino[2,3-b]pyrazin-4-yl]ethyl}acetamide;

N-{2-[3-oxo-2-(trifluoromethyl)-6-({[3-(trifluoromethyl)phenyl]methyl}amino)-4-hydropyridino[2,3-b]pyrazin-4-yl]ethyl}acetamide;

N-{2-[2-methyl-3-oxo-6-({[3-(trifluoromethyl)phenyl]methyl}amino)-4-hydropyridino[2,3-b]pyrazin-4-yl]ethyl}acetamide;

N-[2-(6-{[(3,4-dichlorophenyl)methyl]amino}-2-methyl-3-oxo-4-hydropyridino[2,3-b]pyrazin-4-yl)ethyl]acetamide;

ethyl 3-(6-{[(3,4-dichlorophenyl)methyl]amino}-2-(4-methoxyphenyl)-3-oxo-4-hydropyridino[2,3-b]pyrazin-4-yl)propanoate;

ethyl 4-(6-{[(3,4-dichlorophenyl)methyl]amino}-2-(4-inethoxyphenyl)-3-oxo-4-hydropyridino[2-b]pyrazin-4-yl)butanoate;

3-[3-oxo-2-(3-pyridyl)-6-({[3-(trifluoromethyl)phenyl]methyl}amino)-4-hydropyridino[2,3-b]pyrazin-4-yl]propanamide;

3-(6-{[(3,4-dichlorophenyl)methyl]amino}-3-oxo-2-(3-pyridyl)-4-hydropyridino[2,3-b]pyrazin-4-yl)propanamide;

3-(6-{[(3,4-dichlorophenyl)methyl]amino}-2-(4-methoxyphenyl)-3-oxo-4-hydropyridino[2,3-b]pyrazin-4-yl)propanamide;

3-[2-(4-methoxyphenyl)-3-oxo-6-({[3-(trifluoromethyl)phenyl]methyl}amino)-4-hydropyridino[2,3-b]pyrazin-4-yl]butanamide;

4-(2-hydroxyethyl)-2-(4-methoxyphenyl)-6-({[3-(trifluoromethyl)phenyl]methyl}amino)-4-hydropyridino[3,2-b]pyrazin-3-one; and 3-[2-(4-methoxyphenyl)-3-oxo-6-({[3-(trifluoromethyl)phenyl]methyl}amino)-4-hydropyridino[2,3-b]pyrazin-4-yl]propanamide.

C. Preparation of Compounds of Formula I varying $R^1$, $R^2$, and $R^3$

Similarly, following the procedure of Example 3A above, but optionally substituting other compounds of formula (3) for N-(2-(6-(3,4-dichlorobenzylamino)-3-nitropyridin-2-ylamino)ethyl)acetamide, and optionally substituting other oxoacetate of formula (5) for ethyl 2-(4-methoxyphenyl)-2-oxoacetate, other compounds of Formula I are prepared.

EXAMPLE 4

Preparation of a Compound of Formula I

A. Preparation of a Compound of Formula I in which $W^1$ is CH, $W^2$ is N, $R^1$ is —$CH_2CH_2NH_2$, $R^2$ is 3,4-Dichlorophenyl, and $R^3$ is 4-Methoxyphenyl

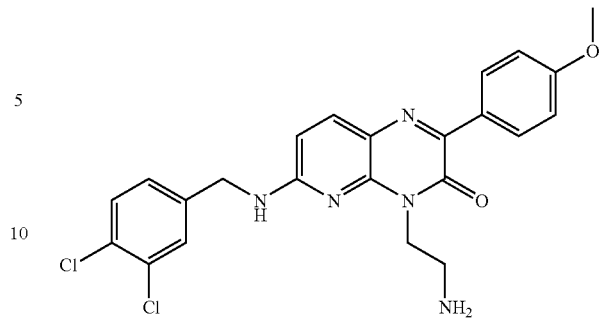

N-[2-(6-{[(3,4-dichlorophenyl)methyl]amino}-2-(4-methoxyphenyl)-3-oxo(4-hydropyridino[2,3-b]pyrazin-4-yl))ethyl](tert-butoxy)carboxamide (150 mg, 0.26 mmol), prepared as described in Example 3, was dissolved in dioxane (1 mL) and reacted with 4N HCl in dioxane (2 mL) at room temperature for 1 hour. The solution turned dark red and precipitate formed. The precipitate was filtered off to provide 4-(2-aminoethyl)-6-{[(3,4-dichlorophenyl)methyl]amino}-2-(4-methoxyphenyl)-4-hydropyridino[3,2-b]pyrazin-3-one as a dark red solid.

B. Preparation of Compounds of Formula I varying $R^2$ and $R^3$

Similarly, following the procedure of Example 4A above, but optionally substituting other compounds of Formula I having protected $R^1$ groups for N-[2-(2-{[(3,4-dichlorophenyl)methyl]amino}-6-(4-methoxyphenyl)-7-oxo(8-hydropteridin-8-yl))ethyl](tert-butoxy)carboxamide, other compounds of Formula I are prepared.

EXAMPLE 5

Preparation of a Compound of Formula

A. Preparation of a Compound of Formula I in which $W^1$ is CH, $W^2$ is N, $R^1$ is —$CH_2CH_2NHCH(O)$, $R^2$ is 3,4-Dichlorophenyl, and $R^3$ is 4-Methoxyphenyl

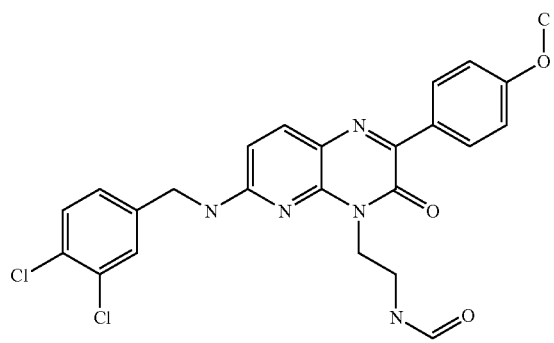

To a suspension of crude 4-(2-aminoethyl)-6-{[(3,4-dichlorophenyl)methyl]amino}-2-(4-methoxyphenyl)-4-hydropyridino[3,2-b]pyrazin-3-one, as prepared in Example 4, (85 mg, 0.17 mmol) was reacted as a suspension in MeCN (2 mL) with diisopropylethylamine (0.07 mL) and methyl formate (0.6 mL) in a microwave vessel at 150° C. for 35 min. After cooling off the mixture was concentrated and residue purified by chromatography (5% MeOH in dichloromethane) to provide N-[2-(6-{[(3,4-dichlorophenyl)methyl]amino}-2-(4-methoxyphenyl)-3-oxo-4-hydropyridino[2,3-b]pyrazin-4-yl)ethyl]carboxamide as a yellow solid.

B. Preparation of Compounds of Formula I varying $R^1$, $R^2$, and $R^3$

Similarly, following the procedure of Example 5A above, but optionally substituting other compounds of Formula I having a terminal $R^1$ amino group for 8-(2-aminoethyl)-2-{[(3,4-dichlorophenyl)methyl]amino}-6-(4-methoxyphenyl)-8-hydropteridin-7-one or optionally replacing methyl formate with other $R^5$ derivatives, the following other compounds of Formula I were prepared:

N-{2-[2-(4-methoxyphenyl)-3-oxo-6-({[3-(trifluoromethyl)phenyl]methyl}amino)-4-hydropyridino[2,3-b]pyrazin-4-yl]ethyl)}carboxamide;

N-[2-(6-{[(3,4-dichlorophenyl)methyl]amino}-3-oxo-2-(3-pyridyl)-4-hydropyridino[2,3-b]pyrazin-4-yl)ethyl]carboxamide; and N-{2-[3-oxo-2-(3-pyridyl)-6-({[3-(trifluoromethyl)phenyl]methyl}amino)-4-hydropyridino[2,3-b]pyrazin-4-yl]ethyl}carboxamide.

C. Preparation of Compounds of Formula I varying $R^1$, $R^2$, and $R^3$

Similarly, following the procedure of Example 5A above, but optionally substituting other compounds of Formula I having a terminal $R^1$ amino group for 842-aminoethyl)-2-{[(3,4-dichlorophenyl)methyl]amino}-6-(4-methoxyphenyl)-8-hydropteridin-7-one or optionally replacing methyl formate with other $R^5$ derivatives other compounds of Formula I are prepared.

EXAMPLE 6

Preparation of a Compound of Formula I

A. Preparation of a Compound of Formula I in which $W^1$ is CH, $W^2$ is N, $R^1$ is —CH$_2$CH$_2$NHCH(O), $R^2$ is 3,4-Dichlorophenyl, and $R^3$ is 4-Methoxyphenyl

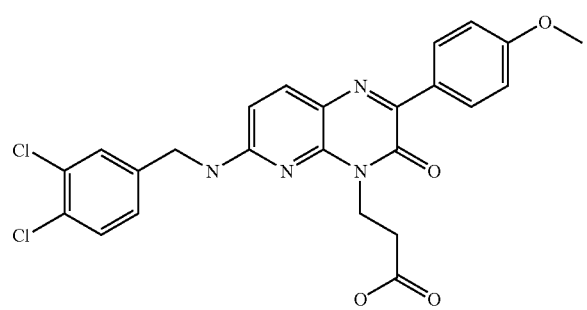

Crude starting material ethyl 3-(6-{[(3,4-dichlorophenyl)methyl]amino}-2-(4-methoxyphenyl)-3-oxo-4-hydropyridino[2,3-b]pyrazin-4-yl)propanoate, as made in Example 3, (20 mg, 0.038 mmol) was reacted with LiOH monohydrate (3.1 mg, 0.077 mmol) in 1:1:1 THF/MeOH/water mixture (20 mL) overnight at room temperature. The reaction was diluted with water and 1N HCl was added to acidify the mixture. The solution was extracted 3 times with EtOAc to afford 3-(6-{[3,4-dichlorophenyl)methyl]amino}-2-(4-methoxyphenyl)-3-oxo-4-hydropyridino[2,3-b]pyrazin-4-yl)propanoic acid after concentration as a yellow solid.

B. Preparation of Compounds of Formula I varying $R^1$, $R^2$, and $R^3$

Similarly, following the procedure of Example 6A above, but optionally substituting other compounds of Formula I having a $R^1$ ester group for ethyl 3-(6-{[(3,4-dichlorophenyl)methyl]amino}-2-(4-methoxyphenyl)-3-oxo-4-hydropyridino[2,3-b]pyrazin-4-yl)propanoate, the following other compound of Formula I was prepared:

4-(6-{[(3,4-dichlorophenyl)methyl]amino}-2-(4-methoxyphenyl)-3-oxo-4-hydropyridino[2,3-b]pyrazin-4-yl)butanoic acid.

C. Preparation of Compounds of Formula I varying $R^1$, $R^2$, and $R^3$

Similarly, following the procedure of Example 6A above, but optionally substituting other compounds of Formula I having a $R^1$ ester group for ethyl 3-(6-{[(3,4-dichlorophenyl)methyl]amino}-2-(4-methoxyphenyl)-3-oxo-4-hydropyridino[2,3-b]pyrazin-4-yl)propanoate, other compounds of Formula I are prepared.

EXAMPLE 7

Characterization of Stearoyl-CoA Desaturase Inhibitor

Materials and Methods

Materials

[$^3$H]stearoyl CoA and sterculic acid were obtained from PerkinElmer and Planta Piloto de Quimica Fina, respectively. Commercial sources of other reagents are listed below:

| Material | Company |
| --- | --- |
| [$^3$H]H$_2$O | PerkinElmer |
| Stearoyl CoA | Sigma |
| CoA | Sigma |
| NADH | Sigma |
| Tris, 1M | Invitrogen |
| MgCl2 | Sigma |
| BSA | Sigma |
| DMSO | Sigma |
| ATP | Sigma |
| 96-well plates | Corning |
| Bio-Beads SM-2 | Bio-Rad |

Preparation of Rat Liver Microsomes

The rat liver microsomes were collected according to the procedure described in Ozols (1990) *Methods Enzm*, 182: 225.

In Vivo Experiment (Liver Perfusion and Collection)

Male Sprague Dawley Rats were placed on regimented fasting protocol for one week to stimulate SCD enzymatic activity. 48-hour periods were alternated between feeding and fasting to induce and down-regulate SCD activity with SCD activity being induced via carbohydrate rich diet prior to liver perfusion and collection.

The rats were anesthetized with Isoflurane inhalation anesthetic, the liver perfused with cold phosphate buffered saline (PBS), weighed, and chilled in cold homogenization buffer (250 mM sucrose, 10 mM Tris, 1 mM EDTA, pH 7.6.

The livers were finely minced and placed in homogenization tube. 40 mL of homogenization buffer was added to the homogenization tube and the liver homogenized and centrifuged in a pre-chilled SLA-600 TC at 800G rotor for 10 min at 4° C.

Following centrifugation, the supernatant was collected and the pellet removed and discarded. This supernatant was then centrifuged at 10,000 G for 35 minutes. Following centrifugation, the supernatant was collected and the pellet discarded. The supernatant was further centrifuged in a pre-chilled 45-Ti rotor at 130,000 G (41,000 RPM) for 90 minutes at 4° C.

In Vitro (Microsomal Collection)

The supernatant was then aspirated off and the collected microsomal pellet washed in 25 mL of Glycerol PBS (1×PBS 7.4, 20% Glycerol) and resuspended in 4-5 volumes of Glycerol PBS.

The protein concentration of the microsomal preparation was determined by BCA assay (Pierce) and the microsomes were aliquoted and stored at −80° C.

Preparation of Hydrophobic Beads

Biobeads were ground to a smaller size in a mortar and pestle and filtered through 300 μM mesh and then resuspended in 3.6% TCA.

Stock Solutions

Stock solutions and their storage conditions are listed below:

| Solution | Storage condition |
| --- | --- |
| 20 mg/ml Stearoyl CoA | −80° C. |
| 2.8 mCi/ml [$^3$H]Stearoyl CoA | −80° C. |
| CoA | freshly prepared |
| Sterculic acid | freshly prepared |
| 0.2 M NADH | −80° C. |
| 1 M Tris, pH 7.2 | room temperature |
| 1 M MgCl2 | room temperature |
| 100 mM ATP | −20° C. |
| 10% BSA | 4° C. |
| 10-20 mg/ml microsome | −80° C. |

The SCD Assay Buffer

SCD was determined in the desaturase assay buffer. This assay buffer contained 0.1 M Tris buffer, pH 7.2, 2 mM NADH, 4.8 mM ATP, 0.5 mM CoA, 4.8 mM MgC12, and 0.1% BSA.

The Procedure for the SCD Assay (Adapted from Talamo and Bloch (1969) *Analytical Biochemistry* 29:300-304)

1 μl of each compound of Formula I was added to an assay plate by a low volume (0.5-104) multichannel pipette. A DMSO control was also prepared. The microsomes were quickly thawed and added to assay buffer so that a concentration of 1-0.1 mg/ml was achieved (0.5-0.05 mg/ml assay final). 500 of the microsome suspension in assay buffer was then added into each well in the compound assay plate, the plate was covered, and the microsomes preincubated with the compounds for 30-60 minutes on the orbital shaker, 50-75 rpm, at room temperature.

After preincubation, the reaction was initiated by the addition of 50 μl of substrate solution (20 μM Stearoyl CoA, [3H]Stearoyl CoA, 74nCi) to the preincubated microsomes/ compound suspensions in MilliQ (Millipore) $H_2O$. The reaction mixtures were then incubated for 45 minutes on the orbital shaker at 50-75 rpm at room temperature.

The reaction was terminated by the addition of 10 μl of 21% tricarboxylic acid (TCA) to the reaction mixture followed incubation on the orbital shaker for 30 minutes at 50-75 rpm at room temperature followed by centrifugation for 5 minutes at 3700 rpm.

500 of a 6% Bio-Bead suspension in $H_2O$ was added to the reaction mixture and the assay plate was sealed. The Bio-Bead mixture was incubated on the orbital shaker for 1 to 24 hours, 100-150 rpm at room temperature, and then the mixture was centrifuged at 2000 g for 5 minutes to pellet the Bio-Beads.

250 of the supernatant was harvested from each well and transferred to a detection plate. 1000 of OptiPhase SuperMix scintillation cocktail (containing sufficient NaOH to neutralize the TCA) was added and the solutions mixed by vigorous shaking (300-400 rpm) for 5 minutes at room temperature. The radioactivity was counted in a MicroBeta scintillation counter in order to determine the activity and $IC_{50}$ values for the compounds of Formula I. Table 1 presents the $IC_{50}$ data for a number of compounds of the invention as determined in the above assay.

TABLE 1

| NUMBER | NAME | $IC_{50}$ μM |
| --- | --- | --- |
| I. | N-[2-(6-{[(3,4-dichlorophenyl)methyl]amino}-2-(4-methoxyphenyl)-3-oxo-4-hydropyridino[2,3-b]pyrazin-4-yl)ethyl]acetamide | 0.16 |
| II. | N-[2-(6-{[(4-fluorophenyl)methyl]amino}-2-(4-methoxyphenyl)-3-oxo-4-hydropyridino[2,3-b]pyrazin-4-yl)ethyl]acetamide | 1.30 |
| III. | N-[2-(6-{[(3-chlorophenyl)methyl]amino}-2-(4-methoxyphenyl)-3-oxo-4-hydropyridino[2,3-b]pyrazin-4-yl)ethyl]acetamide | 0.42 |
| IV. | N-[2-(6-{[(3-chloro-4-fluorophenyl)methyl]amino}-2-(4-methoxyphenyl)-3-oxo-4-hydropyridino[2,3-b]pyrazin-4-yl)ethyl]acetamide | 0.21 |
| V. | 4-(2-aminoethyl)-6-{[(3,4-dichlorophenyl)methyl]amino}-2-(4-methoxyphenyl)-4-hydropyridino[3,2-b]pyrazin-3-one | 2.7 |
| VI. | N-[2-(6-{[(3,4-dichlorophenyl)methyl]amino}-2-(4-methoxyphenyl)-3-oxo-4-hydropyridino[2,3-b]pyrazin-4-yl)ethyl]carboxamide | 0.10 |
| VII. | N-[2-(6-{[(3,4-dichlorophenyl)methyl]amino}-3-oxo-2-(3-pyridyl)-4-hydropyridino[2,3-b]pyrazin-4-yl)ethyl]acetamide | 0.46 |
| VIII. | 3-(6-{[(3,4-dichlorophenyl)methyl]amino}-2-(4-methoxyphenyl)-3-oxo-4-hydropyridino[2,3-b]pyrazin-4-yl)propanamide | 0.19 |
| IX. | N-{2-[2-(4-methoxyphenyl)-3-oxo-6-({[3-(trifluoromethyl)phenyl]methyl}amino)-4-hydropyridino[2,3-b]pyrazin-4-yl]ethyl}acetamide | 0.34 |
| X. | N-{2-[2-(4-methoxyphenyl)-3-oxo-6-({[4-(trifluoromethyl)phenyl]methyl}amino)-4-hydropyridino[2,3-b]pyrazin-4-yl]ethyl}acetamide | 9.40 |

TABLE 1-continued

| NUMBER | NAME | IC$_{50}$ μM |
|---|---|---|
| XI. | N-[2-(6-{[(3,4-dichlorophenyl)methyl]amino}-2-(4-methylthiophenyl)-3-oxo-4-hydropyridino[2,3-b]pyrazin-4-yl)ethyl]acetamide | 0.19 |
| XII. | N-[2-(6-{[(3,4-dichlorophenyl)methyl]amino}-2-(4-methylphenyl)-3-oxo-4-hydropyridino[2,3-b]pyrazin-4-yl)ethyl]acetamide | 0.56 |
| XIII. | N-[2-(6-{[(3-chloro-4-fluorophenyl)methyl]amino}-3-oxo-2-(3-pyridyl)-4-hydropyridino[2,3-b]pyrazin-4-yl)ethyl]acetamide | 0.33 |
| XIV. | ethyl 3-(6-{[(3,4-dichlorophenyl)methyl]amino}-2-(4-methoxyphenyl)-3-oxo-4-hydropyridino[2,3-b]pyrazin-4-yl)propanoate | 3.1 |
| XV. | ethyl 4-(6-{[(3,4-dichlorophenyl)methyl]amino}-2-(4-methoxyphenyl)-3-oxo-4-hydropyridino[2,3-b]pyrazin-4-yl)butanoate | 5.2 |
| XVI. | 4-(6-{[(3,4-dichlorophenyl)methyl]amino}-2-(4-methoxyphenyl)-3-oxo-4-hydropyridino[2,3-b]pyrazin-4-yl)butanoic acid | 7.1 |
| XVII. | 3-(6-{[(3,4-dichlorophenyl)methyl]amino}-2-(4-methoxyphenyl)-3-oxo-4-hydropyridino[2,3-b]pyrazin-4-yl)propanoic acid | 3.2 |
| XVIII. | 3-(6-{[(3,4-dichlorophenyl)methyl]amino}-3-oxo-2-(3-pyridyl)-4-hydropyridino[2,3-b]pyrazin-4-yl)propanamide | 0.18 |
| XIX. | N-[2-(6-([[(3,4-dichlorophenyl)methyl]amino}-3-oxo-2-(3-pyridyl)-4-hydropyridino[2,3-b]pyrazin-4-yl)ethyl]carboxamide | 0.20 |
| XX. | N-{2-[3-oxo-2-(3-pyridyl)-6-({[3-(trifluoromethyl)phenyl]methyl}amino)-4-hydropyridino[2,3-b]pyrazin-4-yl]ethyl}acetamide | 1.40 |
| XXI. | N-[2-(6-{[(3-bromophenyl)methyl]amino}-2-(4-methoxyphenyl)-3-oxo-4-hydropyridino[2,3-b]pyrazin-4-yl)ethyl]acetamide | 1.33 |
| XXII. | N-{2-[6-({[3,5-bis(trifluoromethyl)phenyl]methyl}amino)-2-(4-methoxyphenyl)-3-oxo-4-hydropyridino[2,3-b]pyrazin-4-yl]ethyl}acetamide | 0.36 |
| XXIII. | N-{2-[6-({[4-fluoro-3-(trifluoromethyl)phenyl]methyl}amino)-2-(4-methoxyphenyl)-3-oxo-4-hydropyridino[2,3-b]pyrazin-4-yl]ethyl}acetamide | 0.16 |
| XXIV. | 4-(2-hydroxyethyl)-2-(4-methoxyphenyl)-6-({[3-(trifluoromethyl)phenyl]methyl}amino)-4-hydropyridino[3,2-b]pyrazin-3-one | 1.20 |
| XXV. | N-{2-[2-(4-methoxyphenyl)-3-oxo-6-({[5-(trifluoromethyl)(3-pyridyl)]methyl}amino)-4-hydropyridino[2,3-b]pyrazin-4-yl]ethyl}acetamide | 0.48 |
| XXVI. | N-{2-[2-(4-methoxyphenyl)-3-oxo-6-({[3-(trifluoromethyl)phenyl]methy}amino)-4-hydropyridino[2,3-b]pyrazin-4-yl]ethyl}carboxamide | 0.04 |
| XXVII. | N-{2-[3-oxo-2-(3-pyridyl)-6-({[3-(trifluoromethyl)phenyl]methyl}amino)-4-hydropyridino[2,3-b]pyrazin-4-yl]ethyl}carboxamide | 0.05 |
| XXVIII. | N-{2-[3-oxo-2-(trifluoromethyl)-6-({[3-(trifluoromethyl)phenyl]methyl}amino)-4-hydropyridino[2,3-b]pyrazin-4-yl]ethyl}acetamide | 1.49 |
| XXIX. | N-{2-[2-methyl-3-oxo-6-({[3-(trifluoromethyl)phenyl]methyl}amino)-4-hydropyridino[2,3-b]pyrazin-4-yl]ethyl}acetamide | 0.75 |
| XXX. | N-[2-(6-{[(3,4-dichlorophenyl)methyl]amino}-2-methyl-3-oxo-4-hydropyridino[2,3-b]pyrazin-4-yl)ethyl]acetamide | 0.25 |
| XXXI. | N-[2-(7-{[(3,4-dichlorophenyl)methyl]amino}-2-oxo-3-(3-pyridyl)hydropyridino[3,4-b]pyrazinyl)ethyl]acetamide | 2.25 |
| XXXII. | N-[2-(7-{[(3,4-dichlorophenyl)methyl]amino}-3-(4-methylphenyl)-2-oxohydropyridino[3,4-b]pyrazinyl)ethyl]acetamide | 0.57 |
| XXXIII. | N-[2-(7-{[(3,4-dichlorophenyl)methyl]amino}-3-(4-methoxyphenyl)-2-oxohydropyridino[3,4-b]pyrazinyl)ethyl]acetamide | 0.27 |
| XXXIV. | N-[2-(7-{[(3,4-dichlorophenyl)methyl]amino}-3-(4-chlorophenyl)-2-oxohydropyridino[3,4-b]pyrazinyl)ethyl]acetamide | 0.36 |
| XXXV. | N-[2-(7-{[(3,4-dichlorophenyl)methyl]amino}-3-methyl-2-oxohydropyridino[3,4-b]pyrazinyl)ethyl]acetamide | 0.44 |

TABLE 1-continued

| NUMBER | NAME | IC$_{50}$ µM |
|---|---|---|
| XXXVI. | N-[2-(7-{[(3,4-dichlorophenyl)methyl]amino}-3-(4-methoxyphenyl)-2-oxohydroquinoxalinyl)ethyl]acetamide | 0.11 |
| XXXVII. | N-{2-[3-(4-methoxyphenyl)-2-oxo-7-({[3-(trifluoromethyl)phenyl]methyl}amino)hydroquinoxalinyl]ethyl}acetamide | 0.093 |
| XXXVIII. | N-{2-[2-oxo-3-(3-pyridyl)-7-({[3-(trifluoromethyl)phenyl]methyl}amino)hydroquinoxalinyl]ethyl}acetamide | 0.28 |
| XXXIX. | N-{2-[3-(4-methylphenyl)-2-oxo-7-({[3-(trifluoromethyl)phenyl]methyl}amino)hydroquinoxalinyl]ethyl}acetamide | 0.027 |
| XL. | N-{2-[3-[4-(2-methoxyethoxy)phenyl]-2-oxo-7-({[3-(trifluoromethyl)phenyl]methyl}amino)hydroquinoxalinyl]ethyl}acetamide | 0.11 |
| XLI. | N-{2-[3-methyl-2-oxo-7-({[3-(trifluoromethyl)phenyl]methyl}amino)hydroquinoxalinyl]ethyl}acetamide | 0.16 |
| XLII. | (N-{2-[3-methyl-2-oxo-7-({[3-(trifluoromethyl)phenyl]methyl}amino)hydroquinoxalinyl]ethyl}carbamoyl)methyl acetate | 0.18 |
| XLIII. | 2-hydroxy-N-{2-[3-methyl-2-oxo-7-({[3-(trifluoromethyl)phenyl]methyl}amino)hydroquinoxalinyl]ethyl}acetamide | 0.16 |
| XLIV. | N-{2-[3-(4-ethylphenyl)-2-oxo-7-({[3-(trifluoromethyl)phenyl]methyl}amino)hydroquinoxalinyl]ethyl}acetamide | 0.042 |
| XLV. | N-(2-{3-(3,4-dichlorophenyl)-2-oxo-7-[(phenylmethoxy)carbonylamino]hydroquinoxalinyl}ethyl)acetamide | 1.75 |

We claim:

1. A compound having the structure of Formula I:

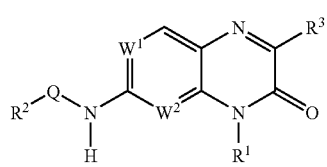

Formula I wherein $R^1$ is a) a 4 to 6 membered nitrogen containing monocyclic heterocycle,
wherein the heterocycle moiety is optionally substituted with from 1 to 3 substituents independently selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, oxo, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl, and
further wherein each optional alkyl, heteroaryl, aryl, and heterocyclyl substituent is further optionally substituted with halo, NO$_2$, alkyl, CF$_3$, amino, mono- or di-alkylamino, alkyl or aryl or heteroaryl amide, NR$^{20}$COR$^{22}$, NR$^{20}$SO$_2$R$^{22}$, COR$^{20}$, CO$_2$R$^{20}$, CON(R$^{20}$)$_2$, NR$^{20}$CON(R$^{20}$)$_2$, OC(O)R$^{20}$, OC(O)N(R$^{20}$)$_2$, S(O)$_3$R$^{20}$, P(O)(OR$^{20}$)$_2$, SR$^{20}$, S(O)R$^{22}$, SO$_2$R$^{22}$, SO$_2$N(R$^{20}$)$_2$, CN, or OR$^{20}$;

b) —X—NR$^4$R$^5$,
c) —X—C(O)NR$^4$R$^5$,
d) —X—C(O)OR$^7$, or
e) —X—OR$^7$ wherein
$R^4$ is hydrogen or $C_{1-4}$ lower alkyl, and
$R^5$ is hydrogen, $C_{1-4}$ lower alkyl, aryl, heteroaryl, —$C_{1-4}$ alkoxy, C(=NH)NH$_2$, —C(=O)R$^6$ or —S(=O)$_2$R$^6$,
wherein
$R^6$ is hydrogen, optionally substituted $C_{1-4}$ alkyl, optionally substituted $C_{2-4}$ alkenyl, $C_{1-4}$ alkoxy, 5 or 6 membered optionally substituted monocyclic aryl, or 5 or 6 membered optionally substituted monocyclic heteroaryl, or
$R^4$ and $R^5$ along with the nitrogen to which they are attached join to form a 5 or 6 membered monocyclic heteroaryl or heterocycle ring;
$R^7$ is hydrogen, optionally substituted $C_{1-4}$ alkyl, optionally substituted $C_{2-4}$ alkenyl, 5 or 6 membered optionally substituted monocyclic aryl, or 5 or 6 membered optionally substituted monocyclic heteroaryl,
X is optionally substituted $C_{2-4}$ linear or branched alkylene;
wherein each R$^6$ and R$^7$ alkyl, alkenyl, aryl and heteroaryl moiety is optionally substituted with from 1 to 3 substituents independently selected from the group consisting of alkyl, heterocyclyl, aryl, heteroaryl, halo, NO$_2$, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, S(O)$_3$R$^{20}$, P(O)(OR$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$, and
further wherein each optional alkyl, heteroaryl, aryl, and heterocyclyl substituent is further optionally substituted with halo, NO$_2$, alkyl, CF$_3$, amino, mono- or di-alkylamino, alkyl or aryl or heteroaryl amide, NR$^{20}$COR$^{22}$, NR$^{20}$SO$_2$R$^{22}$, COR$^{20}$, CO$_2$R$^{20}$, CON(R$^{20}$)$_2$, NR$^{20}$CON(R$^{20}$)$_2$, OC(O)R$^{20}$, OC(O)N(R$^{20}$)$_2$, S(O)$_3$R$^{20}$, P(O)(OR$^{20}$)$_2$, SR$^{20}$, S(O)R$^{22}$, SO$_2$R$^{22}$, SO$_2$N(R$^{20}$)$_2$, CN, or OR$^{20}$;
$R^2$ is optionally substituted aryl, or heteroaryl;
wherein the aryl, heterocyclyl or heteroaryl moiety is optionally substituted with from 1 to 3 substituents independently selected from the group consisting of alkyl, heterocyclyl, aryl, heteroaryl, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $S(O)_3R^{20}$, $P(O)(OR^{20})_2$, $SO_2NR^{20}COR^{22}$, $SO_2NR^{20}CO_2R^{22}$, $SO_2NR^{20}CON(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$, and further wherein each optional alkyl, heteroaryl, aryl, and heterocyclyl substituent is further optionally substituted with halo, $NO_2$, alkyl, $CF_3$, amino, mono- or di-alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $S(O)_3R^{20}$, $P(O)(OR^{20})_2$, $SR^{20}$, $S(O)R^{22}$, $SO_2N(R^{20})_2$, CN, or $OR^{20}$;

$R^3$ is hydrogen, optionally substituted $C_{1-4}$ alkyl, 5 or 6 membered optionally substituted monocyclic cycloalkyl, 5 or 6 membered optionally substituted monocyclic aryl, 5 or 6 membered optionally substituted monocyclic heterocycle, or 5 or 6 membered optionally substituted monocyclic heteroaryl;

wherein the alkyl, cycloalkyl, aryl, heterocyclyl or heteroaryl moiety is optionally substituted with from 1 to 3 substituents independently selected from the group consisting of alkyl, heterocyclyl, aryl, heteroaryl, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $S(O)_3R^{20}$, $P(O)(OR^{20})_2$, $SO_2NR^{20}COR^{22}$, $SO_2NR^{20}CO_2R^{22}$, $SO_2NR^{20}CON(R^{20})_2$, $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$, and further wherein each optional alkyl, heteroaryl, aryl, and heterocyclyl substituent is further optionally substituted with halo, $NO_2$, alkyl, $CF_3$, amino, mono- or di-alkylamino, alkyl or aryl or heteroaryl amide, $NR^{20}COR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $S(O)_3R^{20}$, $P(O)(OR^{20})_2$, $SR^{20}$, $S(O)R^{22}$, $SO_2R^{22}$, $SO_2N(R^{20})_2$, CN, or $OR^{20}$;

$R^{20}$ and $R^{22}$ are independently selected from the group consisting of hydrogen, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl moieties are optionally substituted with from 1 to 3 substituents independently selected from halo, alkyl, mono- or dialkylamino, alkylamide, arylamide, or heteroarylamide, CN, O—$C_{1-6}$ alkyl, $CF_3$, aryl, and heteroaryl;

Q is $C_{1-4}$ alkylene which may optionally contain one or more —NH—, —O—, —S—, or carbonyl linking moieties;

or a pharmaceutically acceptable salt or ester thereof.

2. The compound of claim 1, wherein $R^1$ is —X—C(O)$NR^4R^5$ and $R^3$ is 5 or 6 membered optionally substituted monocyclic aryl.

3. The compound of claim 1, wherein $R^1$ is —X—C(O)$NR^4R^5$ and $R^3$ is 5 or 6 membered optionally substituted monocyclic heterocyclyl.

4. The compound of claim 1 wherein $R^1$ is a 4 to 6 membered nitrogen containing monocyclic heterocycle.

5. The compound of claim 1, wherein $R^1$ is —X—$NR^4R^5$ and $R^3$ is 5 or 6 membered optionally substituted monocyclic aryl.

6. The compound of claim 5, selected from the group consisting of:
N-[2-(7-{[(3,4-dichlorophenyl)methyl]amino}-3-(4-methoxyphenyl)-2-oxohydroquinoxalinyl)ethyl]acetamide;
N-{2-[3-(4-methoxyphenyl)-2-oxo-7-({[3-(trifluoromethyl)phenyl]methyl}amino)hydroquinoxalinyl]ethyl}acetamide;
N-{2-[3-(4-methylphenyl)-2-oxo-7-({[3-(trifluoromethyl)phenyl]methyl}amino)hydroquinoxalinyl]ethyl}acetamide;
N-{2-[3-[4-(2-methoxyethoxy)phenyl]-2-oxo-7-({[3-(trifluoromethyl)phenyl]methyl}amino)hydroquinoxalinyl]ethyl}acetamide;
N-{2-[3-(4-ethylphenyl)-2-oxo-7-({[3-(trifluoromethyl)phenyl]methyl}amino)hydroquinoxalinyl]ethyl}acetamide;
N-(2-{3-(3,4-dichlorophenyl)-2-oxo-7-[phenylmethoxy)carbonylamino]hydroquinoxalinyl}ethyl)acetamide; and
N-(2-{3-(4-methoxyphenyl)-2-oxo-7-[phenylmethoxy)carbonylaminol]hydroquinoxalinyl}ethyl)acetamide.

7. The compound of claim 1, wherein $R^1$ is —X—$NR^4R^5$, —X—C(O)$NR^4R^5$, —X—C(O)$OR^7$, or —X—$OR^7$ and $R^2$ is optionally substituted 5 or 6 membered monocyclic aryl or heteroaryl.

8. The compound of claim 7, wherein $R^1$ is —X—$NR^4R^5$ and $R^3$ is hydrogen.

9. The compound of claim 7, wherein $R^1$ is —X—C(O)$OR^7$ and $R^3$ is 5 or 6 membered optionally substituted monocyclic aryl.

10. The compound of claim 7, wherein $R^1$ is —X—$OR^7$.

11. The compound of claim 7, wherein $R^1$ is —X—$NR^4R^5$ and $R^3$ is 5 or 6 membered optionally substituted monocyclic heteroaryl.

12. The compound of claim 11, namely
N-{2-[2-oxo-3-(3-pyridyl)-7-({[3-(trifluoromethyl)phenyl]methyl}amino)hydroquinoxalinyl]ethyl}acetamide.

13. The compound of claim 7, wherein $R^3$ is optionally substituted $C_{1-4}$ alkyl.

14. The compound of claim 13, selected from the group consisting of:
N-{2-[3-methyl-2-oxo-7-({[3-(trifluoromethyl)phenyl]methyl}amino)hydroquinoxalinyl]ethyl}acetamide;
(N-{2-[3-methyl-2-oxo-7-({[3-(trifluoromethyl)phenyl]methyl}amino)hydroquinoxalinyl]ethyl}carbamoyl)methyl acetate;
2-hydroxy-N-{2-[3-methyl-2-oxo-7-({[3-(trifluoromethyl)phenyl]methyl}amino)hydroquinoxalinyl]ethyl}acetamide; and
4-[2-methyl-3-oxo-6-({[3-(trifluoromethyl)phenyl]methyl}amino)-4-hydropyridino[2,3-b]pyrazin-4-yl]butanamide.

15. A pharmaceutical composition comprising a therapeutically effective amount of the compound of claim 1 or a pharmaceutically acceptable salt or ester thereof.

* * * * *